United States Patent [19]
Coller et al.

[11] Patent Number: 5,976,532
[45] Date of Patent: Nov. 2, 1999

[54] METHOD OF ANTITHROMBOTIC THERAPY USING ANTI-GPIIB/IIIA ANTIBODIES OR FRAGMENTS THEREOF, INCLUDING C7E3

[75] Inventors: Barry S. Coller, Dix Hills, N.Y.; David M. Knight, Paoli, Pa.

[73] Assignee: Centocor, Inc., Malvern, Pa.

[21] Appl. No.: 08/443,374

[22] Filed: May 17, 1995

Related U.S. Application Data

[62] Division of application No. 08/375,074, Jan. 17, 1995, Pat. No. 5,770,198, which is a continuation of application No. 07/771,656, Oct. 4, 1991, abandoned, which is a continuation-in-part of application No. 07/195,720, May 18, 1988, abandoned.

[51] Int. Cl.$^6$ .......................... A61K 39/395; A61K 38/49; C07K 16/28; C12N 9/64
[52] U.S. Cl. ...................................... 424/133.1; 424/130.1; 424/134.1; 424/141.1; 424/143.1; 424/152.1; 424/153.1; 424/173.1; 424/94.63; 424/94.64; 435/212; 435/215; 435/216; 530/387.1; 530/387.3; 530/388.1; 530/388.22; 530/388.25; 530/388.7
[58] Field of Search .............................. 424/130.1, 133.1, 424/134.1, 143.1, 152.1, 173.1, 141.1, 153.1, 94.63, 94.64; 514/2, 7, 8; 530/387.1, 387.3, 388.1, 388.22, 388.25, 388.2, 388.7; 435/215, 212, 216

[56] References Cited

U.S. PATENT DOCUMENTS

| | | |
|---|---|---|
| 4,772,585 | 9/1988 | Sarnoff et al. .............................. 514/2 |
| 4,816,567 | 3/1989 | Cabilly et al. . |
| 5,049,132 | 9/1991 | Shaffer et al. .......................... 604/101 |
| 5,114,842 | 5/1992 | Plow et al. .............................. 424/85.8 |
| 5,225,181 | 7/1993 | Srivastava et al. . |
| 5,275,812 | 1/1994 | Gold et al. . |
| 5,284,751 | 2/1994 | Frelinger, III et al. ................ 435/7.21 |
| 5,318,899 | 6/1994 | Scarborough et al. ................ 435/69.6 |
| 5,336,618 | 8/1994 | Coller . |
| 5,387,413 | 2/1995 | Coller . |
| 5,440,020 | 8/1995 | Coller . |
| 5,446,132 | 8/1995 | Reed et al. .............................. 530/350 |
| 5,462,752 | 10/1995 | Chao et al. .............................. 424/532 |
| 5,470,738 | 11/1995 | Frelinger, III et al. ............ 435/240.27 |
| 5,492,890 | 2/1996 | Ginsberg et al. ......................... 514/12 |
| 5,578,704 | 11/1996 | Kim et al. .......................... 530/388.22 |

FOREIGN PATENT DOCUMENTS

| | | |
|---|---|---|
| 1297816 | 3/1992 | Canada . |
| 0171496 | 2/1986 | European Pat. Off. . |
| 0205270 | 12/1986 | European Pat. Off. . |
| 0206532 | 12/1986 | European Pat. Off. . |
| 0206533 | 12/1986 | European Pat. Off. . |
| 61-47500 | 3/1986 | Japan . |
| 62-29995 | 2/1987 | Japan . |
| 62-30728 | 2/1987 | Japan . |
| WO 86/01533 | 3/1986 | WIPO . |
| WO 89/11538 | 11/1989 | WIPO . |
| WO 90/11783 | 10/1990 | WIPO . |
| WO 92/12734 | 8/1992 | WIPO . |
| WO 93/06863 | 4/1993 | WIPO . |
| WO 95/12412 | 5/1995 | WIPO . |

OTHER PUBLICATIONS

Marx, J.L., "Antibodies Made to Order," *Science*, 229:455–456 (1985).

Dillman, R.O., "Human Antimouse and Antiglobulin Responses to Monoclonal Antibodies," *Antibod., Immunoconj., Radiopharm.*, 3(1):1–15 (1990).

Bovsun, M., "Breakthrough Trial Gives First Hope for Restenosis Drugs," *Biotechnology Newswatch*, pp. 1, 3–4 (Apr. 18, 1994).

Rote, W.E. et al., "Prevention of Rethrombosis After Coronary Thrombolysis in a Chronic Canine Model. I. Adjunctive Therapy with Monoclonal Antibody 7E3 F(ab')$_2$ Fragment," *J. Cardiovasc. Pharm.*, 23:194–202 (1994).

Charo, I.F. et al., "Platelet glycoproteins IIb and IIIa: Evidence for a family of immunologically and structurally related glycoproteins in mammalian cells," *Proc. Natl. Acad. Sci. USA*, 83:8351–8355 (1986).

Coller, B.S. et al., "Platelet Vitronectin Receptor Expression Differentiates Iraqi–Jewish from Arab Patients with Glanzmann Thrombasthenia in Israel," *Blood*, 77 (1):75–83 (1991).

Smith, J.W. et al., "Building Synthetic Antibodies as Adhesive Ligands for Integrins," *J. Biol. Chem.*, 269 (52):32788–32795 (1994).

Asch, E. and E. Pocak, "Vitronectin Binds to Activated Human Platelets and Plays a Role in Platelet Aggregation," *J. Clin. Invest.*, 85:1372–1378 (1990).

Felding, B. and D.A. Cheresh, "Vitronectin and its receptors," *Current Biol.*, 5:864–868 (1993).

Brooks, P.C. et al., "Requirement of Vascular Integrin $\alpha_v\beta_3$ for Angiogenesis," *Science*, 264:569–572 (1994).

"Scripps Research Scientists Develop New Technique for Treating Malignant Tumors," *Genetic Eng. News*, 15 (2): 1 (1995).

Brooks, P.C. et al., "Integrin $\alpha_v\beta_3$ Antagonists Promote Tumor Regression by Inducing Apoptosis of Angiogenic Blood Vessels," *Cell*, 79: 1157–1164 (1994).

Leavesley, D.I. et al., "Integrin β1– and β3–mediated Endothelial Cell Migration is Triggered through Distinct Signalling Mechanisms," *J. Cell. Biol.*, 121 (1):163–170 (1993).

(List continued on next page.)

*Primary Examiner*—Christina Y. Chan
*Assistant Examiner*—Phillip Gambel
*Attorney, Agent, or Firm*—Hamilton, Brook, Smith & Reynolds, P.C.

[57] ABSTRACT

Platelet-specific, chimeric immunoglobulin and immunoglobulin fragments are described. The chimeric molecules are made up of a nonhuman antigen binding region and a human constant region. Preferred immunoglobulins are specific for glycoprotein IIb/IIIa receptor in its complexed form; they block ligand binding to the receptor and prevent platelet aggregation. The immunoglobulins are useful in antithrombotic therapy when administered alone or in conjunction with thrombolytic agents, as well as in thrombus imaging.

24 Claims, 8 Drawing Sheets

OTHER PUBLICATIONS

Ikeda, T. et al., "Osteopontin mRNA is Expressed by Smooth Muscle–derived Foam Cells in Human Atherosclerotic Lesions of the Aorta," *J. Clin. Invest.*, 92: 2814–2820 (1993).

Liaw, L. et al., "The Adhesive and Migratory Effects of Osteopontin are Mediated via Distinct Cell Surface Integrins. Role of $\alpha_v\beta_3$ in Smooth Muscle Cell Migration to Osteopontin In Vitro," *J. Clin. Invest.*, 95: 713–724 (1995).

Nip, J. et al., "Coordinated Expression of the Vitronectin Receptor and the Urokinase–type Plasminogen Activator Receptor in Metastatic Melanoma Cells," *J. Clin. Invest.*, 95: 2096–2103 (1995).

Charo, I.F. et al., "Platelet Glycoprotein IIb–IIIa–like Proteins Mediate Endothelial Cell Attachment to Adhesive Proteins and the Extracellular Matrix," *J. Biol. Chem.*, 262(21): 9935–9938 (1987).

Morrison, S.L. et al., "Chimeric human antibody molecules: Mouse antigen–binding domains with human constant region domains", *Proc. Natl. Acad. Sci. USA*, 81: 6851–6855 (1984).

McEver, R.P. and M.N. Martin, "A Monoclonal Antibody to a Membrane Glycoprotein Binds Only to Activated Platelets", *J. Biol. Chem.*, 259(15): 9799–9804 (1984).

Sun, L.K. et al., "Chimeric antibody with human constant regions and mouse variable regions directed against carcinoma–associated antigen 17–1A", *Proc. Natl. Acad. Sci. USA*, 84: 214–218 (1987).

Coller, B. et al., "A Murine Monoclonal Antibody That completely Blocks the Binding of Fibrinogen to Platelets Produces a Thrombasthenic–like State in Normal Platelets and Binds to Glycoproteins IIb and/or IIIa", *J. Clin. Invest.*, 72: 325–338 (1983).

Hanson, S.R. et al., "Effects of Monoclonal Antibodies against the Platelet Glycoprotein IIb/IIIa Complex on Thrombosis and Hemostasis in the Baboon", *J. Clin. Invest.*, 81: 149–158 (1988).

Pidard, D. et al., "Interaction of AP–2, a Monoclonal Antibody Specific for the Human Platelet Glycoprotein IIb–IIIa Complex, with Intact Platelets", *J. Biol. Chem.*, 258(20): 12,582–12,586 (1983).

Vermylen, J. et al., "Role of Platelet Activation and Fibrin Formation in Thrombogenesis", *J. Am. Coll. Cardiol.*, 8: 2B–9B (1986).

Sahagan, B.G. et al., "A Genetically Engineered Murine/Human Chimeric Antibody Retains Specificity for Human Tumor–Associated Antigen", *J. Immunol.*, 137(3): 1066–1074 (1986).

Coller, B.S. and L.E. Scudder, "Inhibition of Dog Platelet Function by In Vivo Infusion of F(ab')$_2$ Fragments of a Monoclonal Antibody to the Platelet Glycoprotein IIb/IIIa Receptor", *Blood*, 66(6): 1456–1459 (1985).

Coller, B.S. et al., "Antithrombotic Effect of a Monoclonal Antibody to the Platelet Glycoprotein IIb/IIIa Receptor in an Experimental Animal Model", *Blood*, 68(3): 783–786 (1986).

Gold, H.K. et al., "Rapid and sustained coronary artery recanalization with combined bolus injection of recombinant tissue–type plasminogen activator and monoclonal antiplatelet GPIIb/IIIa antibody in a canine preparation", *Circulation*, 77(3): 670–677 (1988).

Yasuda, T. et al., "Monoclonal Antibody against the Platelet Glycoprotein (GP) IIb/IIIa Receptor Prevents Coronary Artery Reocclusion after Reperfusion with Recombinant Tissue–type Plasminogen Activator in Dogs", *J. Clin. Invest.*, 81: 1284–1291 (1988).

Coller, B.S. et al., "Inhibition of Human Platelet Function in Vivo with a Monoclonal Antibody", *Ann. Intern. Med.*, 109: 635–638 (Oct., 1988).

Mickelson, J.K. et al., "Antiplatelet Monoclonal F(ab')$_2$ Antibody Directed Against the Platelet GPIIb/IIIa Receptor Complex Prevents Coronary Artery Thrombosis in the Canine Heart", *J. Mol. Cell. Cardiol.*, 21: 393–405 (1989).

Coller, B.S. et al., "Abolition of In Vivo Platelet Thrombus Formation in Primates With Monoclonal Antibodies to the Platelet GPIIb/IIIa Receptor", *Circulation*, 80(6): 1766–1774 (1989).

Gold et al., "Pharmacodynamic Study of F(ab')$_2$ Fragments of Murine Monoclonal Antibody 7E3 Directed against Human Platelet Glycoprotein IIb/IIIa in Patients with Unstable Angina Pectoris", *J. Clin. Invest.*, 86: 651–659 (Aug. 1990).

Jordan, R.E. et al., "Evaluation of the Potency and Immunogenicity of 7E3 F(ab')$_2$ and Fab Fragments in Monkeys", *Circulation*, 82 (Suppl. III): III–661, Abstract No. 2627 (1990).

Yasuda, T. et al., "Lysis of Plasminogen Activator–Resistant Platelet–Rich Coronary Artery Thrombus With Combined Bolus Injection of Recombinant Tissue–Type Plasminogen Activator and Antiplatelet GPIIb/IIIa Antibody", *J. Am. Coll. Cardio.l*, 16: 1728–1735 (1990).

Bhattacharya, S., et al., "Chimerization of Monoclonal Antibody 7E3 Preserves the GPIIB/IIIA Receptor Blockade and Platelet Functional Inhibition of Murine 7E3", *Clin. Res.*, 39(2):196A (1991).

Ellis et al., "Prospects for the Use of Antagonists to the Platelet Glycoprotein IIb/IIIa Receptor to Prevent Postangioplasty Restenosis and Thrombosis", *J. Am. Coll. Cardiol.*, 17(6): 89B–95B (1991).

Coller et al., "Monoclonal Antibodies to Platelet Glycoprotein IIb/IIIa as Antithrombotic Agents", *Ann. N.Y. Acad. Sci.*, 614: 193–213 (1991).

Machin, S.J. et al., "Comparison of Clinical Efficacy of Murine and Chimeric 7E3 Monoclonal Antibodies on Platelet Function", *Thromb. Haemostas.*, 65(6): 1180, Abstract No. 1746 (1991).

Bhattacharya, S. et al., "Chimeric (humanised) monoclonal antiplatelet antibody 7E3 produces prolonged dose–dependent inhibition of platelet function", *Eur. Heart J.*, 12 (Abstr. Suppl.): 26, Abstract No. 238 (1991).

Tcheng, J.E. et al., "Chimeric Antiplatelet GPIIb/IIIa Receptor Antibody (C–7E3) in Elective PTCA: Safety and Platelet Function Inhibition", *Circulation*, 84(4) (Suppl. II): II–590, Abstract No. 2344 (1991).

Klieman, N.S. et al., "Profound Platelet Inactivation with 7E3 Shortly After Thrombolytic Therapy for Acute Myocardial Infarction: Preliminary Results of the TAMI 8 Trial", *Circulation*, 84(4) (Suppl. II): II–522, Abstract No. 2076 (1991).

Bruggemann, M. et al., "The Immunogenicity of Chimeric Antibodies", *J. Exp. Med.*, 70: 2153–2157 (1989).

LoBuglio, A.F. et al., "Mouse/human chimeric monoclonal antibody in man: Kinetics and immune response", *Proc. Natl. Acad. Sci. USA*, 86: 4220–4224 (1989).

Khazaeli, M.B. et al., "Pharmacokinetics and Immune Response of $^{131}$I–Chimeric Mouse/Human B72.3 (Human γ4) Monoclonal Antibody in Humans", *Cancer Res.*, 51: 5461–5466 (1991).

Benjamin, R.J. et al., "Tolerance to Rat Monoclonal Antibodies, Implications for Serotherapy", *J. Exp. Med.*, 163: 1539–1552 (1986).

Herlyn, D. et al., "Specific Detection of Anti–Idiotypic Immune Responses in Cancer Patients Treated with Murine Monoclonal Antibody", *J. Immunol. Methods*, 85: 27–38 (1985).

Shawler, D.L. et al., "Human Immune Response to Multiple Injections of Murine Monoclonal IgG," *J. Immunol.* 135(2): 1530–1535 (1985).

Chatenoud, L. et al., "Restriction of the Human in vivo Immune Response Against the Mouse Monoclonal Antibody OKT3", *J. Immunol.* 137(3): 830–838 (1986).

Morrison, S.L. et al., "Genetically Engineered Antibody Molecules: New Tools for Cancer Therapy", *Cancer Investigation* 6(2): 185–192 (1988).

Verrill, H. et al., "Clinical Trial of Wistar Institute 17–1A Monoclonal Antibody in Patients with Advanced Gastrointestinal Adenocarcinoma: A Preliminary Report," *Hybridoma*, 5 (Suppl. 1) S175–S183 (1986).

Jordan, R.E. et al. "A Dramatic Reduction of the Immunogenicity of the Anti–GPIIb/IIIa Monoclonal Antibody, 7E3 Fab, by Humanization of the Murine Constant Domains," *Circulation*, 83 Suppl. I): I–411, Abstract No. 1637 (1992).

Trang, J.M. et al., "Pharmacokinetics of a Mouse/Human Chimeric Monoclonal Antibody (C–17–1A) in Metastatic Adenocarcinoma Patients," *Pharm. Res.*, 7(6): 587–592 (1990).

Meredith, R.F. et al., "Pharmacokinetics, Immune Response, and Biodistribution of Iodine–131–Labeled Chimeric Mouse/Human IgG1,k 17–1A Monoclonal Antibody," *J. Nuc. Med.*, 32(6): 1162–1168 (1991).

Lobuglio, A.F. et al., "Chimeric Monoclonal Antibody Studies in Colo–Rectal Cancer," Epenetos, A.A. (ed.) In: *Advances in the Applications of Monoclonal Antibodies in Clinical Oncology* Chapt. 33 (Chapman & Hall: London) pp. 291–295 (1991).

Dillman, R.O., "Human Antimouse and Antiglobulin Responses to Monoclonal Antibodies," *Antibody, Immunoconjugates and Radiopharmaceuticals*, 3(1): 1–15 (1990) (presented at the 4th Int'l Conf. on Monoclonal Antibody Immunoconjugates for Cancer, San Diego, CA, Mar. 30, 1989).

Williams, G., "Novel Antibody Reagents: Production and Potential," *Tibtech*, 6: 36–40 (1988).

Marx, J.L., "Antibodies Made to Order," *Science*, 229: 455–456 (1985).

Riechmann, L. et al., "Reshaping Human Antibodies for Therapy," *Nature*, 332: 323–327 (1988).

Jordan, R.E. et al., "Evaluation of the Potency and Immunogenicity of 7E3 F(ab')$_2$ and Fab Fragments in Monkeys", *Circulation*, 82 (Suppl. III): Abstract No. 2627 (1990).

Wagner, C.L. et al., "Molecular Pharmacology of Chimeric 7E3 Monoclonal Fab Fragment Binding to Platelet GPIIb/IIIa Receptors", *Atherosclerosis and Thrombosis*, 11: 1594a (1991).

Simoons, M.L., et al., "Chimeric 7E3 Antiplatelet Antibody Fab for Treatment of Refractory Unstable Angina: A Placebo–Controlled Pilot Study", *J. Am. Coll. Cardiol.*, 21(2): 269A, Abstract No. 768–1 (1993).

Rote, W., et al., "Prevention of Carotid Artery Thrombosis: Effects of c7E3 Fab, Aspirin and/or Heparin in Cynomolgus Monkeys," *Cardiovascular Drugs and Therapy*, 7 (Suppl. 2): 459, Abstract No. 353 (1993).

Iuliucci, J.D., et al., "Anti–platelet Activity and Safety of Chimeric Anti–platelet Monoclonal Antibody 7E3 Fab Combined with Streptokinase and Anticoagulant Drugs," *Circulation*, 84(4) (Suppl. II): II–247, Abstract No. 0983 (1991).

Kohmura, C., et al., "A Novel Chimeric Human–murine GPIIb–IIIa Antiplatelet Antibody Enhances Thrombolysis in the Baboon," *J. Am. Coll. Cardiol.*, 21(2) (Suppl. A): 85A, Abstract No. 867–22 (1993).

Christopoulos, C., et al., "Flow Cytometric Observations on the in vivo use of Fab Fragments of a Chimaeric Monoclonal Antibody to Platelet Glycoprotein IIb–IIIa," *Blood Coagulation and Fibrinolysis*, 4: 729–737 (1993).

Topol, E.J., et al., "Randomised Trial of Coronary Intervention with Antibody Against Platelet IIb/IIIa Integrin for Reduction of Clinical Restenosis: Results at Six Months," *Lancet*, 343: 881–886 (1994).

Coller, B.S., "A New Murine Monoclonal Antibody Reports an Activation–dependent Change in the Conformation and/or Microenvironment of the Platelet Glycoprotein IIb/IIa Complex," *J. Clin. Invest.*, 76: 101–108 (1985).

Ellis, S.G. et al., "Antiplatelet GPIIb/IIIa (7E3) Antibody in Elective PTCA: Safety and Inhibition of Platelet Function," *Circulation*, 82 (Suppl. III): III–191, Abstract No. 0755 (1990).

Oster, Z.H. et al., "Thrombus Radioimmunoscintigraphy: An Approach Using Monoclonal Antiplatelet Antibody", *Proc. Natl. Acad. Sci. USA*, 82: 3465–3468 (1985).

Goding, J.W., *Monoclonal Antibodies: Principles and Practice*, (Academic Press, Inc.: Orlando, FL), pp. 118–120 (1983).

Morrison, S.L., "Transfectomas Provide Novel Chimeric Antibodies", *Science*, 229: 1202–1207 (1985).

Harris, W.J. and S. Emery, "Therapeutic Antibodies—The Coming of Age", *Tibtech*, 11:42–44 (1993).

Harker, L., "Role of Platelets and Thrombosis in Mechanisms of Acute Occlusion and Restenosis After Angioplasty", *Am. J. Cardiol.*, 60:20B–28B (1987).

Paul (Ed) Fundamental Immunology Raven Press 1993 NY p. 242 only.

Knight et al. Molecular Immunol. 32 : 1271–1281 (1995).

Co et al. J. Immunol. 152: 2968–2976 (1994).

Coller et al. Thrombosis Haemostasis 74:302–308 (1993).

Genetts Ann. Pharmacother. 30: 251–7 (1996).

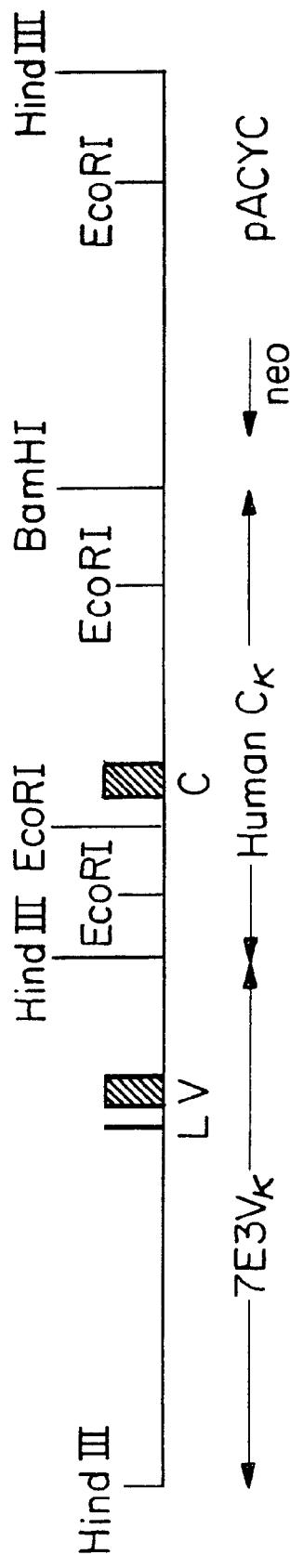
FIG. 1A p7E3V$_K$hC$_K$
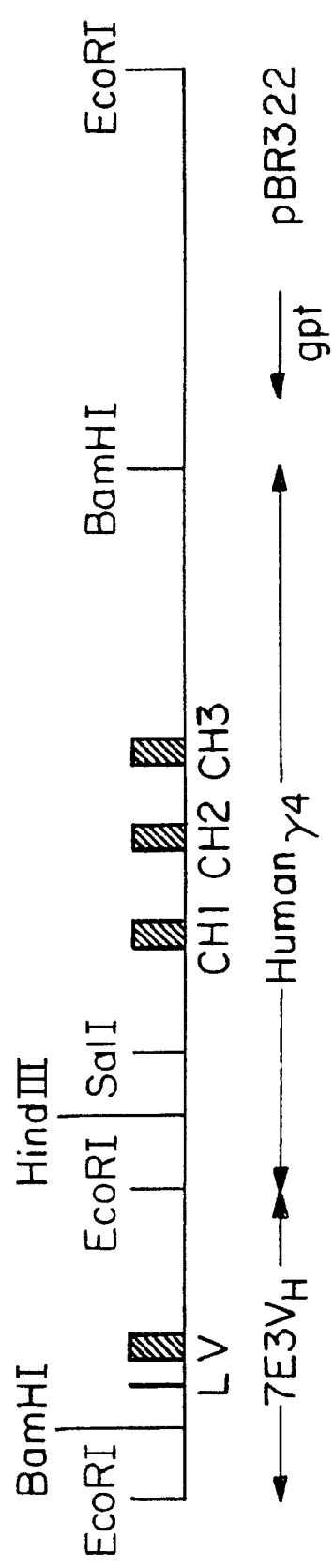
FIG. 1B p7E3V$_H$hC$_{\gamma4}$

METHOD OF ANTITHROMBOTIC THERAPY USING ANTI-GPIIB/IIIA ANTIBODIES OR FRAGMENTS THEREOF, INCLUDING C7E3

RELATED APPLICATIONS

This application is a division of application Ser. No. 08/375,074 filed Jan. 17, 1995 now U.S. Pat. No. 5,770,198, which is a File Wrapper Continuation of Ser. No. 07/771,656, filed Oct. 4, 1991 now abandoned, which is a Continuation-in-Part of Ser. No. 07/195,720, filed May 18, 1988 now abandoned.

BACKGROUND OF THE INVENTION

Platelet aggregation is an essential event in the formation of blood clots. Under normal circumstances, blood clots serve to prevent the escape of blood cells from the vascular system. However, during certain disease states, clots can restrict or totally occlude blood flow resulting in cellular necrosis.

For example, platelet aggregation and subsequent thrombosis at the site of an atherosclerotic plaque is an important causative factor in the genesis of conditions such as angina, acute myocardial infarction, and reocculusion following successful thrombolysis and angioplasty. Heart attack patients are typically treated with thrombolytic agents such as tissue plasminogen activator or streptokinase, which dissolve the fibrin component of clots. A major complication associated with fibrinolysis is reocclusion based on platelet aggregation which can result in further heart damage. Since glycoprotein (GP)IIb/IIIa receptors are known to be responsible for platelet aggregation, reagents which block these receptors are expected to reduce or prevent reocclusion following thrombolytic therapy and to accelerate the rate of thrombolysis. Such reagents are also expected to be useful in therapy of other vaso-occlusive and throboembolic disorders.

One approach to blocking platelet aggregation involves monoclonal antibodies specific for GPIIb/IIIa receptors. A murine monoclonal antibody, designated 7E3, that inhibits platelet aggregation and appears useful in the treatment of human thrombotic diseases is described in published European Patent Application Nos. 205,207 and 206,532. It is known in the art that murine antibodies have characteristics which may severely limit their use in human therapy. As foreign proteins, murine antibodies may elicit immune reactions that reduce or destroy their therapeutic efficacy and/or evoke allergic or hypersensitivity reactions in patients. The need for readministration of such therapeutic modalities in thromboembolic disorders increases the likelihood of these types of immune reactions.

Chimeric antibodies consisting of non-human binding regions joined to human constant regions have been suggested as a means to circumvent the immunoreactivity problems of murine antibodies. See $Proc.\ Natl.\ Acad.\ Sci.\ USA$, 81:6851 (1984) and PCT Application No. PCT/GB85 00392. Since the constant region is largely responsible for immunoreactivity of an antibody molecule, chimeric antibodies with constant regions of human origin should be less likely to evoke an anti-murine response in humans. However, it is unpredictable whether the joining of a human constant region to a murine binding region of a desired specificity will reduce immunoreactivity and/or alter the binding capability of the resulting chimeric antibody.

SUMMARY OF THE INVENTION

This invention pertains to a platelet-specific chimeric immunoglobulin comprising a variable or antigen binding region of non-human origin and a constant region of human origin. The chimeric immunoglobulins can be specific for GPIIb/IIIa receptor or other platelet components. These antibodies bind to platelets and can block platelet aggregation and thus are useful as antithrombotic agents and to prevent or reduce reocclusion following thrombolysis.

BRIEF DESCRIPTION OF THE FIGURES

FIGS. 1A–1B are schematic representations of the plasmids $p7E3V_\kappa hC_\kappa$ and $p7E3V_H hC_{G4}$, which carry the chimeric gene constructs encoding the light and heavy chains, respectively, of a chimeric 7E3 immunoglobulin.

DETAILED DESCRIPTION OF THE INVENTION

Figure 2:
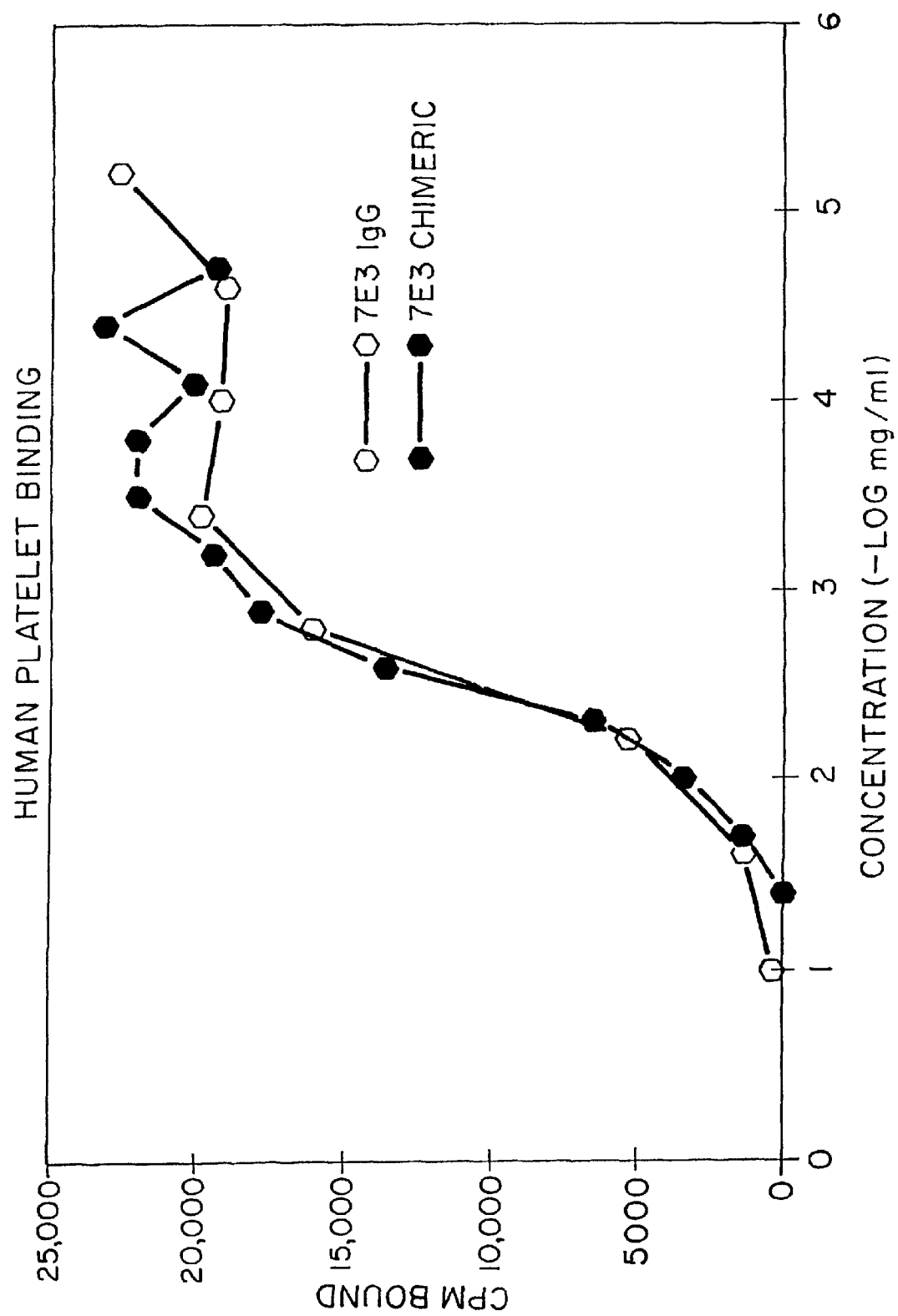
FIG. 2 shows the binding of the chimeric 7E3 immunoglobulin encoded by vectors $p7E3V_\kappa hC_\kappa$ and $p7E3V_H hC_{G4}$ to platelets.

The chimeric immunoglobulins of the present invention are comprised of individual chimeric heavy and light immunoglobulin chains. The chimeric heavy chain is comprised of an antigen-binding region derived from the heavy chain of a non-human antibody specific for platelets (e.g., specific for the GPIIb/IIIa receptor) linked to a human heavy chain constant region. The chimeric light chain comprises an antigen binding region derived from the light chain of the non-human antibody linked to a human light chain constant region.

The present immunoglobulins can be monovalent, divalent or polyvalent. Monovalent immunoglobulins are dimers (HL) formed of a chimeric heavy chain associated through disulfide bridges with a chimeric light chain. Divalent immunoglobulins are tetramers ($H_2L_2$) formed of two dimers associated through at least one disulfide bridge. Polyvalent immunoglobulins can also be produced, for example, by employing a heavy chain constant region that aggregates (e.g., μ heavy chain constant regions). Chimeric immunoglobulin fragments such as Fab, Fab' or F(ab')$_2$ can also be produced.

The non-human antigen binding regions of the chimeric immunoglobulin are derived from immunoglobulins specific for platelets. Preferred immunoglobulins are specific for platelet GPIIb/IIIa receptors and can block ligand binding to the glycoprotein IIb/IIIa receptor complex.

Thrombosis begins with the adhesion of platelets at sites of vessel wall injury. The adhesion of platelets is mediated by platelet surface receptors which bind to extracellular matrix proteins in the exposed subendothelium, such as von Willebrand factor, collagen, fibronectin, vitronectin, and laminin. Platelet adhesion results in a monolayer of platelets. Subsequently, platelet activation occurs in response to agonists such as epinephrine, ADP, collagen, and thrombin. Activation leads to the exposure of the glycoprotein IIb/IIIa receptor (GPIIb/IIIa) on the platelet surface. GPIIb/IIIa on activated platelets is then available to bind to fibrinogen, which can mediate platelet aggregation. The binding of GPIIb/IIIa to other adhesive proteins, such as von Willebrand factor can also cause platelet cross-linking and aggregation. Thus, the binding of adhesive molecules, such as fibrinogen or von Willebrand factor, to GPIIb/IIIa to cause aggregation of platelets is a common step in thrombus formation, making the GPIIb/IIIa receptor an attractive target for therapeutic agents which can interfere with the interaction of GPIIa/IIIb with these molecules. Furthermore, by use of an anti-GPIIb/IIIa chimeric antibody, the aggregation of activated platelets is expected to be inhibited, without interfering with the initial adhesion of platelets. This selective inhibition of platelet aggregation may be desirable because platelet adhesion, without aggregation, may contribute to maintaining hemostasis.

Examples of suitable antibodies specific for platelets include 7E3 and 10E5. See European Patent Application Nos. 205,207 and 206,532, the teachings of which are incorporated herein. The 7E3 antibody (or antibody reactive with the same or a functionally equivalent epitope) is especially preferred because it is specific for the the complexed form of the GPIIb/IIIa receptor. Other antibodies specific for the GPIIb/IIIa receptor (antigen recognized by 7E3), such as those specific for either the IIb or IIIa components, can also be used. Antibodies specific for other platelet antigens can be employed. For example, antibodies reactive with platelet α granule membrane protein GMP-140 such as S12 antibody (*J. Biol. Chem.* 259:9799–9804 (1984)) can be used.

Preferably, the antigen binding region will be of murine origin because murine antibodies against platelets and particularly, GPIIb/IIIa receptors, are available or can be produced in murine systems. Other animal or rodent species provide alternative sources of antigen binding regions.

The constant regions of the chimeric antibodies are derived from human immunoglobulins. The heavy chain constant region can be selected from any of the five isotypes alpha, delta, epsilon, gamma or mu. Further, heavy chains of various subclasses (such as the IgG subclasses of heavy chains) are responsible for different effector functions and thus, by choosing the desired heavy chain constant region, chimeric antibodies with desired effector function can be produced. Preferred constant regions are gamma 1 (IgG1), gamma 3 (IgG3) and gamma 4 (IgG4). The light chain constant region can be of the kappa or lambda type.

In general, the chimeric antibodies are produced by preparing, for each of the light and heavy chain components of the chimeric immunoglobulin, a fused gene comprising a first DNA segment that encodes at least the functional portion of the platelet-specific variable region of nonhuman origin linked (e.g., functionally rearranged variable region with joining segment) to a second DNA segment encoding at least a part of a human constant region. Each fused gene is assembled in or inserted into an expression vector. Recipient cells capable of expressing the gene products are then transfected with the genes. The transfected recipient cells are cultured under conditions that permit expression of the incorporated genes and the expressed immunoglobulins or immunoglobulin chains are recovered.

Genes encoding the variable region of Ig light and heavy chains can be obtained from lymphoid cells that produce the platelet-specific antibodies. For example, the hybridoma cell lines that produce antibody against the GPIIb/IIIa receptor provide a source of immunoglobulin variable region for the present chimeric antibodies. Other rodent cell lines are available. Cell lines can be produced by challenging a rodent with a human platelet or a GPIIb/IIIa receptor-containing component or fraction of platelet, forming fused hybrid cells between antibody-producing cells and a myeloma cell line, cloning the hybrid and selecting clones that produce antibody against platelet or glycoprotein IIb/IIIa receptor.

Constant regions can be obtained from human antibody-producing cells by standard cloning techniques. Alternatively, because genes representing the two classes of light chains and the five classes of heavy chains have been cloned, constant regions of human origin are readily available from these clones. Chimeric antibody binding fragments such as F(ab')$_2$ and Fab fragments can be prepared by designing a chimeric heavy chain gene in truncated form. For example, a chimeric gene encoding a F(ab')$_2$ heavy chain portion would include DNA sequences encoding the $CH_1$ domain and hinge region of the heavy chain. Alternatively, such fragments can be obtained by enzymatic cleavage of a chimeric immunoglobulin. For instance, papain or pepsin cleavage can generate Fab or F(ab')$_2$ fragments, respectively.

Preferably, the fused genes encoding the light and heavy chimeric chains (or portions thereof) are assembled in two different expression vectors that can be used to cotransfect a recipient cell. Each vector contains two selectable genes—one for selection in a bacterial system and one for selection in a eukaryotic system—each vector having a different pair of genes. These vectors allow production and amplification of the fused genes in bacterial systems, and subsequent cotransfection of eukaryotic cells and selection of the cotransfected cells. Examples of selectable genes for the bacterial system are the genes that confer ampicillin resistance and the gene that confers chloramphenicol resistance. Two selectable genes for selection of eukarytoic transfectants are preferred: (i) the xanthine-guanine phosphoribosyltransferase gene (gpt), and (ii) the phosphotransferase gene from Tn5 (designated neo). Selection with gpt is based on the ability of the enzyme encoded by this gene to use xanthine as a substrate for purine nucleotide synthesis; the analogous endogenous enzyme cannot. In a medium containing xanthine and mycophenolic acid, which blocks the conversion of inosine monophosphate to xanthine monophosphate, only cells expressing the gpt gene can survive. The product of the neo blocks the inhibition of protein synthesis in eukarytoic cells caused by the antibiotic G418 and other antibiotics of its class. The two selection procedures can be used simultaneously or sequentially to select for the expression of immunoglobulin chain genes introduced on two different DNA vectors into a eukaryotic cell.

The preferred recipient cell line is a myeloma cell. Myeloma cells can synthesize, assemble and secrete immunoglobulins encoded by transfected Ig genes. Further, they possess the mechanism for glycosylation of the immunoglobulin. A particularly preferred recipient cell is a Ig-nonproducing myeloma cell line such as Sp2/0. These cell lines produce only the immunoglobulin encoded by the transfected immunoglobulin genes. Myeloma cells can be grown in culture or in the peritoneum of mice where secreted immunoglobulin can be obtained from ascites fluid. Other lymphoid cells such as B lymphocytes or hybridoma cells can serve as suitable recipient cells.

Several methods exist for transfecting lymphoid cell with vectors containing immunoglobulin encoding genes. A preferred way of introducing DNA into lymphoid cells is by electroporation. In this procedure recipient cells are subjected to an electric pulse in the presence of the DNA to be incorporated. See e.g., Potter et al., *Proc. Natl. Acad. Sci. USA* 81:7161 (1984). Another way to introduce DNA is by protoplast fusion. In this method, lysozyme is used to strip cell walls from bacteria harboring the recombinant plasmid containing the chimeric Ig gene. The resulting spheroplasts are fused with myeloma cells with polyethylene glycol. After protoplast fusion, the transfectants are selected and isolated. Another technique that can be used to introduce DNA into many cell types is calcium phosphate precipitation.

The chimeric immunoglobulin genes can also be expressed in nonlymphoid cells such as bacteria or yeast. When expressed in bacteria, the immunoglobulin heavy chains and light chains become part of inclusion bodies. Thus, the chains must be isolated and purified and then assembled into functional immunoglobulin molecules. Other strategies for expression in *E. coli* are available (see e.g., Pluckthun, A., *Bio/Technology* 9: 545–551 (1991); Skerra, A. et al., *Bio/Technology* 9:273–278 (1991)), including secretion from *E. coli* as fusion proteins comprising a signal sequence.

Utility of Platelet-specific Chimeric Immunoglobulin

The chimeric platelet-specific antibodies of this invention are useful as antithrombotic therapeutic agents. The chimeric antibodies (or fragments thereof) can be used to inhibit platelet aggregation and thrombus formation. The antibodies can also be used to inhibit cyclic flow variations which are caused by platelet aggregation, and which may precede thrombus formation or reformation. The antibodies can be used in a variety of situations where thrombus formation or reformation (reocclusion) is to be prevented. For instance, the antibody can be administered to an individual (e.g., a mammal such as a human) to prevent thrombosis in pulmonary embolism, transient ischemic attacks (TIAs), deep vein thrombosis, coronary bypass surgery, surgery to insert a prosthetic valve or vessel (e.g., in autologous, non-autologous or synthetic vessel graft). The antibodies of the present invention can also be administered to an individual to prevent platelet aggregation and thrombosis in angioplasty procedures performed by balloon, coronary atherectomy, laser angioplasty or other suitable methods. Antibody can be administered prior to the angioplasty procedure (pre-angioplasty), during angioplasty, or post-angioplasty. Such treatment can prevent thrombosis and thereby reduce the rate of thrombotic complications following angioplasty, such as death, myocardial infarction, or recurrent ischemic events necessitating PTCA or coronary bypass surgery.

For instance as shown in Example 4, administration of a chimeric anti-platelet antibody (chimeric 7E3 Fab fragment) as adjuvant therapy prior to angioplasty (percutaneous transluminal coronary angioplasty, PTCA) increased bleeding times and reduced agonist-induced platelet aggregation as assayed by ex vivo platelet aggregation assays. The results of the experiments reported in Examples 4 and 5 also suggest that blockade of platelet GPIIb/IIIa and inhibition of aggregation by c7E3 antibody (an Fab fragment) translates into in vivo antithrombotic efficacy in humans.

The aggregation of platelets activates the coagulation cascade and produces a more stable fibrin meshwork and occlusive clot, which can be lysed by thrombolytic agents. The antibody can be administered to an individual (e.g., a human) alone or in conjunction with a thrombolytic agent, such as as a plasminogen activator (e.g., tissue plasminogen activator, urokinase, or streptokinase, recombinant tissue plasminogen activator) or an anticoagulant or anti-platelet agent, such as aspirin, heparin, or a coumarin anticoagulant (e.g., warfarin), to prevent or reduce reocclusion that can occur after thrombolysis and to accelerate clot lysis. The antibody or fragment can be administered before, along with or subsequent to administration of the thrombolytic agent or anticoagulant, in amounts sufficient to prevent platelet aggregation that can result in reocclusion.

An effective amount (e.g., an amount sufficient for inhibition of platelet aggregation and thereby of inhibition of thrombus formation) of the antibody or antibody fragment can be given parenterally, preferably intravenously, in a pharmaceutically acceptable vehicle such as sterile saline. Buffered media may be included. The antibody formulation can contain additional additives, such as a stabilizer (e.g., Polysorbate 80, USP/NF). The antibody can be administered in a single dose, continuously, or in multiple infusions (e.g., a bolus injection, followed by continuous infusion). Alternatively, the antibody could be administered by a controlled release mechanism (e.g., by a polymer or patch delivery system) or by another suitable method. The amount to be administered will depend on a variety of factors such as the clinical symptoms, weight of the individual, whether other drugs (e.g., thrombolytic agents) are administered.

During repeat therapy with anti-platelet antibodies, drug-induced thrombocytopenia may occur; this may be a result of the body recognizing the antibody-coated platelets as foreign proteins, raising antibodies against them, and then clearing them via the reticuloendothelial system more rapidly than normal. Because of the uniquely high density of the GPIIb/IIIa receptor on the platelet surface (~80,000 receptors per platelet) and the large number of platelets in the circulation (~0.25 –0.5×10$^6$ per $\mu$l), thrombocytopenia may be an important complication of treatment with anti-platelet antibodies. The use of a chimeric anti-platelet (e.g., anti-GPIIb/IIIa) antibody can avoid this problem. It is predicted that the majority of the murine component of the chimeric antibody will be bound to the platelet (e.g., via the GPIIb/IIIa receptor) and thus will be inaccessible to the immune system, rendering the chimeric antibody functionally indistinguishable from a human antibody directed against the same epitope. Therefore, the chimeric antibody is expected to be non-immunogenic in spite of the murine antigen binding region. In addition, the chimeric anti-platelet antibodies of the present invention may minimize (reduce or prevent) the thrombocytopenia which might otherwise occur on administration of an anti-platelet antibody.

The platelet-specific chimeric immunoglobulins of this invention are also useful for thrombus imaging. For this purpose, antibody fragments are generally preferred. As described above, chimeric heavy chain gene can be designed in truncated form to produce a chimeric immunoglobulin fragment (e.g., Fab, Fab', or F(ab')$_2$) for immunoscintigraphic imaging. These molecules can be labeled either directly or through a coupled chelating agent such as DTPA, with radioisotopes such as $^{131}$Iodine, $^{125}$Iodine, $^{99m}$Technetium or $^{111}$Indium to produce radioimmunoscintigraphic agents. Alternatively, a radiometal binding (chelating) domain can be engineered into the chimeric antibody site to provide a site for labeling. Thus, a chimeric immunoglobulin can be designed as a protein that has a nonhuman platelet-specific variable region, a human constant region (preferably truncated), and a metal binding domain derived from a metal binding protein, such as metallothionein.

The platelet-specific chimeric immunoglobulin is administered to a patient suspected of having thrombus. After sufficient time to allow the labeled immunoglobulin to localize at the thrombus site, the signal generated by the label is detected by a photoscanning device such as a gamma camera. The detected signal is then converted to an image of the thrombus. The image makes it possible to locate the thrombus in vivo and to devise an appropriate therapeutic strategy.

The invention is further described by the following examples, wherein all parts and percentages are by weight, and degrees are Celsius unless otherwise stated.

EXEMPLIFICATION

Example 1

Production of Chimeric Platelet Specific IgG4

A. General Strategy

The strategy for cloning the variable regions for the heavy and light chain genes from the 7E3 hybridoma was based upon the linkage in the genome between the variable region and the corresponding J (joining) region for functionally rearranged (and expressed) Ig genes. J region DNA probes can be used to screen genomic libraries to isolate DNA linked to the J regions; DNA in the germline configuration (unrearranged) would also hybridize to J probes but is not linked to a variable region sequence and can be identified by restriction enzyme analysis of the isolated clones.

The cloning strategy, therefore, was to isolate variable regions from rearranged heavy and light chain genes using $J_H$ and $J_K$ probes. These clones were tested to see if their sequences were expressed in the 7E3 hybridoma by Northern analysis. Those clones that contained expressed sequences were put into expression vectors containing human constant regions and transfected into mouse myeloma cells to determine if an antibody was produced. The antibody from producing cells was then tested for binding specificity and functionality in comparison with the 7E3 murine antibody.

A deposit of cell line derivative, murine hybridoma 7E3, was made with the American Type Culture Collection, 10801 University Boulevard, Manassas, Va. 20110-2209, May 30, 1985. The accession number HB8832 was assigned after successful viability testing.

B. Materials and Methods

Heavy Chain Genomic Library Construction

To isolate the heavy chain variable region gene from the 7E3 hybridoma, a size-selected genomic library was constructed using the phage lambda vector gt10. Southern analysis of Eco RI digested 7E3 DNA using a $J_H$ probe revealed a single 3.5 kb band corresponding to a rearranged heavy chain locus. It was likely that this fragment contained the 7E3 heavy chain variable region gene. High molecular weight DNA was isolated from 7E3 hybridoma cells and digested to completion with restriction endonuclease Eco RI. The DNA was then fractionated on a 0.7% agarose gel and the DNA of size range 3–4 kb was isolated directly from the gel. After phenol/chloroform extraction and fractionation using a Sephadex® G-50 gel filtration column, the 3–4 kb fragments were ligated with lambda gt10 arms (Promega Biotech, Inc) and packaged into phage particles in vitro using Packagene® packaging system from Promega Biotech. This library was screened directly at a density of approximately 30,000 plaques per 150 mm petri dish using a $^{32}$P-labeled $J_H$ probe. Plaque hybridizations were carried out in 5×SSC, 50% formamide, 2×Denhardt's reagent, 200 μg/ml denatured salmon sperm DNA at 42 degrees C. for 18–20 hours. Final washes were in 0.5×SSC, 0.1% SDS at 65 degrees. Positive clones were identified after autoradiography.

Light Chain Genomic Library Construction

To isolate the variable region gene for the 7E3 light chain, a genomic library was constructed in the lambda vector EMBL-3. High molecular weight DNA was partially digested with restriction endonuclease Sau3A and size-fractionated on a 10–40% sucrose density gradient. DNA fragments of 18–23 kb were ligated with EMBL-3 arms and packaged into phage particles in vitro using Packagene® packaging system. This library was screened at a density of 30,000 plaques per 150 mm plate using a $J_K$ probe. Hybridization and wash conditions were identical to those used for the heavy chain library.

DNA Probes

The mouse heavy chain $J_H$ probe is a 2 kb BamHI/EcoRI fragment containing both J3 and J4 segments. The mouse light chain $J_K$ probe is a 2.7 kb HindIII fragment containing all five $J_K$ segments. $^{32}$P-labeled probes were prepared by nick translation using a kit obtained from Amersham, Inc. Free nucleotides were removed by centrifugation through a Sephadex® G-50 column. The specific activities of the probes were approximately $10^9$ cpm/μg.

Northern Analysis

15 μg total cellular RNA was subjected to electrophoresis on 1% agarose/formaldehyde gels (Maniatis, et al, Molecular Cloning) and transferred to nitrocellulose. Blots were hybridized with nick translated DNA probes in 50% formamide, 2×Denhardt's solution, 5×SSC, and 200 μg/ml denatured salmon sperm DNA at 42 degrees for 10 hours. Final wash conditions were 0.5×SSC 0.1% SDS at 65 degrees.

DNA Transfection using Electroporation

Plasmid DNA to be transfected was purified by centrifuging to equilibrium in ethidium bromide/cesium chloride gradients two times. 10–50 μg of plasmid DNA was added to 8>10⁶ SP2/0 cells in PBS on ice and the mixture placed in a Biorad electroporation apparatus. Electroporation was at 200 volts and the cells were plated out in 96 well microtiter plates. Appropriate drug selection was applied after 48 hours and drug resistant colonies were identified after 1–2 weeks.

Quantitation of Antibody Production

Tissue culture supernatant was analyzed for IgG protein content by particle concentration fluorescence immunoassay (Jolley, M. E. et al, (1984) *J. Immunol. Meth.* 67:21) using standard curves generated with purified IgG. Concentration of chimeric 7E3 antibody with human constant regions was determined using goat antihuman IgG Fc antibody-coated polystyrene beads and fluorescein conjugated goat anti-human IgG Fc antibody. The assay was carried out with an automated instrument (Pandex Laboratories, Inc.)

Purification of Platelet-specific Chimeric IgG4 Antibody

Tissue culture supernatant was concentrated with a Diaflo YM100 ultrafiltration membrane (Amicon), and loaded onto a protein A-Sepharose® column. The chimeric antibody was eluted from the protein A column with a sodium citrate pH gradient from pH 6.5 to pH 3.5. The purified antibody was concentrated using a Diaflo YM100 ultrafiltration membrane. Antibody concentration was measured by determining the absorbance at 280 nm.

Binding Inhibition Assay

Purified antibody (either murine 7E3 or chimeric 7E3) was used to compete with radioiodinated 7E3 antibody for binding to human platelets. Platelet-rich plasma (PRP) was prepared by centrifugation of citrated whole human blood at 1875 rpm for 3.5 minutes. $^{125}$I-labeled 7E3 antibody (150,000 cpm) was added to the appropriate dilution of the purified test antibody and the reaction was initiated by the addition of 150 μl PRP. Incubation was for 1–2 hours at room temperature and the platelets with bound antibody were separated from free antibody by centrifugation through 30% sucrose at 12,000 g for 4 minutes in a 0.4 ml microfuge tube. The tube tip containing the platelet/antibody pellet was cut off and counted in a gamma counter. The competition for binding to platelets between iodinated 7E3 and chimeric 7E3 was compared to the competition between iodinated 7E3 and unlabeled 7E3 IgG.

Inhibition of Platelet Aggregation

Purified 7E3 or chimeric 7E3 antibody was added to citrated whole human blood and incubated at 37 degrees for 10 minutes. The rate of platelet aggregation was measured after activation with collagen or ADP using a whole blood aggregometer (Chronolog Corp.).

C. Results

Cloning of the Platelet-specific Variable Gene Regions

Several positive clones were isolated from the heavy and light chain libraries after screening approximately one million plaques using the $J_H$ and $J_\kappa$ probes, respectively. Following at least three rounds of plaque purification, bacteriophage DNA was isolated for each positive clone, digested with either EcoRI (heavy chain clones) or HindIII (light chain clones) and fractionated on 1% agarose gels. The DNA was transferred to nitrocellulose and the blots were hybridized with $J_H$ (heavy chain) or $J_\kappa$ $^{32}$P-labeled DNA probes. For the heavy chain, 2 clones were obtained that contained 3.5 kb Eco RI DNA fragments that hybridized to the $J_H$ probe. Two size classes of HindIII fragments of 3.0 and 6.0 kb were identified with the $J_\kappa$ probe.

Cloned DNA corresponding to the authentic heavy and light chain variable regions from the 7E3 hybridoma should hybridize to mRNA isolated from the hybridoma. Non-functional DNA rearrangements at either the heavy or light chain loci should not be expressed. Northern analysis demonstrated that the 3.5 kb EcoRI putative heavy chain fragment and the 6.0 kb HindIII putative light chain fragment each hybridizes to the appropriate size mRNA from the 7E3 hybridoma. The subcloned fragments were labeled with $^{32}$P by nick translation and hybridized to northern blots containing total RNA derived from SP2/0 (the fusion partner of the 7E3 hybridoma) or from 7E3. The 3.5 kb EcoRI heavy chain fragment hybridized with a 2 kb mRNA in 7E3 RNA but not in SP2/0 RNA. Similarly, the 6.0 kb light chain HindIII fragment hybridized with a 1250 bp mRNA in 7E3 RNA but not in SP2/0 RNA. These are the correct sizes for heavy and light chain mRNAs, respectively. Because the cloned DNA fragments contain sequences expressed in the 7E3 hybridoma, these data suggest that the clones contain the correct variable region sequences from the 7E3 hybridoma. The final functional test, however, is the demonstration that these sequences, when combined with appropriate constant region sequences, are capable of directing the synthesis of an antibody with a specificity and affinity similar to that of the murine 7E3 antibody.

Vectors and Expression Systems

The putative light and heavy chain V genes cloned from the 7E3 hybridoma were joined to human κ and G4 constant region genes in expression vectors described previously (Sun, L. et al., *Proc. Natl. Acad. Sci. USA* 84:214–218 (1987). The 17-1A $V_\kappa$ HindIII fragment of pSV184ΔHneo17-1AV$_\kappa$hC$_\kappa$ was replaced with the 6.0 kb HindIII fragment corresponding to the putative light chain variable region gene from 7E3. Similarly, the 17-1A $V_H$ Eco RI fragment of pSV2ΔHgpt17-1AV$_H$-hC$_{G4}$ was replaced with the 3.5 kb EcoRI fragment corresponding to the putative heavy chain V region gene from 7E3. The structures of the resulting plasmids, designated p7E3V$_\kappa$hC$_{H\kappa}$ and p7E3V$_H$hC$_{G4}$, are shown in FIGS. 1A–1B.

To express the chimeric heavy and light chain genes, the two plasmids were cotransfected into the nonproducing mouse myeloma cell line SP2/0. The light chain plasmid confers resistance to G418 and the heavy chain plasmid confers resistance to mycophenolic acid, thus allowing a double selection to be used to obtain clones carrying and expressing genes from each plasmid. Colonies resistant to G418 and mycophenolic acid were expanded to stable cell lines and maintained in the presence of both drugs. Tissue culture supernatant from these cell lines was tested for antibody using a particle concentration fluorescence immunoassay with polystyrene beads coated with goat anti-human IgG Fc antibody and the same antibody labeled with fluorescein. Out of the first 10 lines checked, one (designated c-7E3F6) that produced approximately 2 μg/ml was selected for further study.

Platelet Binding Activity Assay

After purification of c-7E3F6 antibody using a protein A-Sepharose® column, the antibody was concentrated and compared to murine 7E3 IgG in the platelet binding activity assay. FIG. 2 shows that murine 7E3 and c-7E3F6 (the putative chimeric antibody) compete with radiolabeled 7E3 for platelet binding to the same extent; the binding curves are superimposable indicating that the binding characteristics of murine and chimeric 7E3 are identical by this criterion.

Inhibition of Platelet Aggregation by c-7E3F6

Figure 3:
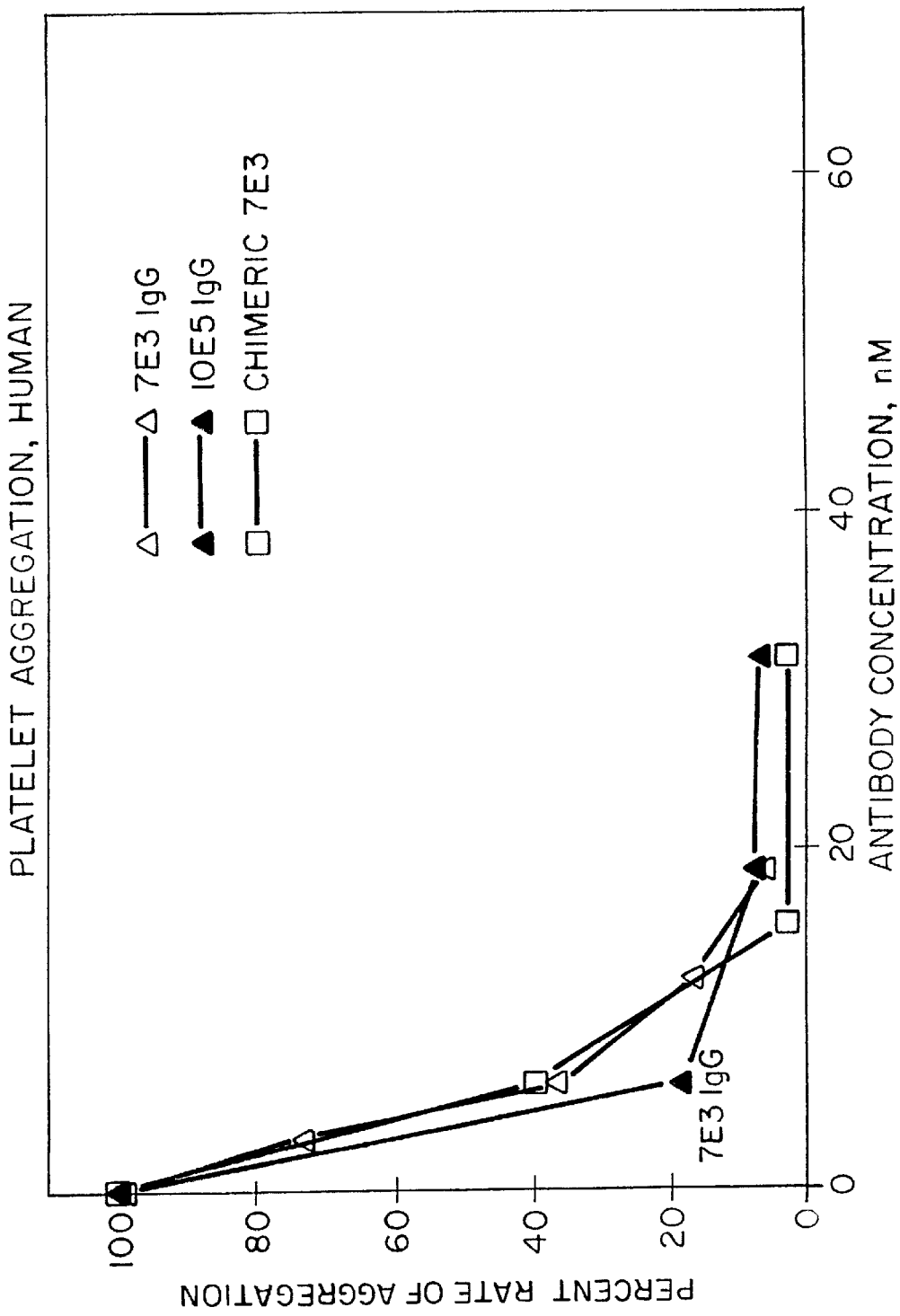
FIG. 3 shows the inhibition of platelet aggregation by a chimeric 7E3 (c7E3) immunoglobulin.

Purified c-7E3F6 was compared to murine 7E3 in a functional assay that measures the ability of the test antibody to inhibit aggregation of human platelets. The results of such an assay are shown in FIG. 3 and demonstrate that both antibodies inhibit collagen-induced platelet aggregation to the same extent at the same antibody concentration. c-7E3F6 also inhibits ADP-induced platelet aggregation to a similar extent.

The results of the platelet binding assay and the inhibition of platelet aggregation assay demonstrate that: (1) the correct variable region genes were indeed cloned from the 7E3 hybridoma; and (2) the substitution of the human constant regions for the murine constant regions has no effect on the binding or functional characteristics of the 7E3 variable regions as measured by these assays.

Fibrinogen-coated Bead Assay

The chimeric c-7E3F6 antibody was found positive in a qualitative, functional assay that measures the ability of an antibody to inhibit the agglutination between platelets and fibrinogen-coated beads. Coller, B. et al. (1983) *J. Clin. Invest.* 73:325–338.

Example 2

Production of Chimeric IgG1 and IgG3

The DNA segment encoding the variable region of the heavy chain from the murine 7E3 antibody was linked to the human γ1 and γ3 constant regions present on the expression vectors pSV2ΔHgpt17-1AV$_H$-hC$_{G1}$ and pSV2ΔHgpt17-1AV$_H$-hC$_{G3}$ (Sun et al., *Proc. Natl. Acad. Sci. USA* 84:214–218, 1987), by replacing the 17-1A heavy or light chain variable region fragments with the corresponding 7E3 variable region fragments. The resulting chimeric heavy chain genes were cotransfected with the chimeric light chain gene into SP2/0 cells to generate stable cell lines secreting γ1,K, and γ3,K antibodies.

Example 3

Initial Studies of Use of Chimeric 7E3 Fab in Humans

Preparation of Chimeric 7E3 Fab Fragments

The Fab fragment of chimeric 7E3 (c7E3) was produced by enzymatic digestion of purified chimeric 7E3 IgG (gamma 1 heavy chain, kappa light chain) with the proteolytic enzyme papain. The Fab fragment was isolated by a series of purification steps designed to yield a product which was free of other digestion fragments and other contaminating components (e.g., protein, nucleic acid, viruses). The final product was prepared as a sterile, non-pyrogenic solution containing 2 mg of monoclonal chimeric 7E3 Fab per ml of 0.15 M sodium chloride, 0.01 M sodium phosphate, pH7.2. In certain preparations, polysorbate 80 was included at a final concentration of 0.001% (w/v). Prior to use, the product was filtered through a 0.22 micron low protein binding filter. The product was stored at 2–8° C.

Pharmacokinetics: Plasma Clearance of c7E3 Fab in Humans

The plasma clearance of chimeric 7E3 (c7E3) Fab fragment was studied in three patients with stable coronary disease. Following a 0.25-mg/kg dose of c7E3 Fab administered intravenously as a five minute infusion, blood samples were taken at various times from two minutes to 72 hours. It was anticipated that a certain portion of the antibody would exist in an unbound state in plasma. To quantify this unbound antibody component, it was necessary to rapidly separate the plasma from the platelets to prevent further binding ex vivo. The plasma concentration of free c7E3 Fab was measured by solid-phase enzyme immunoassay (EIA). The assay employed affinity isolated anti-murine 7E3 IgG purified from rabbit antisera for solid-phase capture and a detection system based on a biotinylated derivative of the same rabbit anti-7E3 antibody preparation. The results are presented in Table 1.

TABLE 1

PLASMA CONCENTRATION OF c7E3 Fab IN PATIENTS TREATED WITH A 0.25-MG/KG DOSE

| | c7E3 Fab (µg/mL) | | |
| --- | --- | --- | --- |
| Time* | Patient A | Patient B | Patient C |
| Pre-dose | ND | ND | ND |
| 2 min | NA | 2.554 | 2.312 |
| 5 min | 1.149 | 1.873 | 1.411 |
| 10 min | 0.714 | 1.331 | 1.111 |
| 15 min | 0.610 | 0.916 | 0.852 |
| 20 min | 0.499 | 0.985 | 0.756 |
| 30 min. | 0.464 | 0.815 | 0.515 |
| 45 min | 0.340 | 0.704 | 0.405 |
| 1 hr | 0.309 | 0.437 | 0.195 |
| 2 hr | 0.288 | 0.262 | 0.149 |
| 6 hr | 0.204 | 0.095 | 0.105 |
| 12 hr | 0.112 | 0.072 | 0.064 |
| 24 hr | 0.065 | 0.058 | 0.046 |
| 48 hr | 0.055 | 1.47 | 0.175 |
| 72 hr | 0.196 | ND | 0.076 |

*Interval between end of infusion and blood drawing. Note that platelets were in contact with the plasma for an additional 2 minutes after the blood was drawn (i.e., for the time required to separate the plasma by centrifugation).
ND = Not detected/below the detectable level of the assay (0.025 µg/mL).
NA = Not available.

Figure 4:
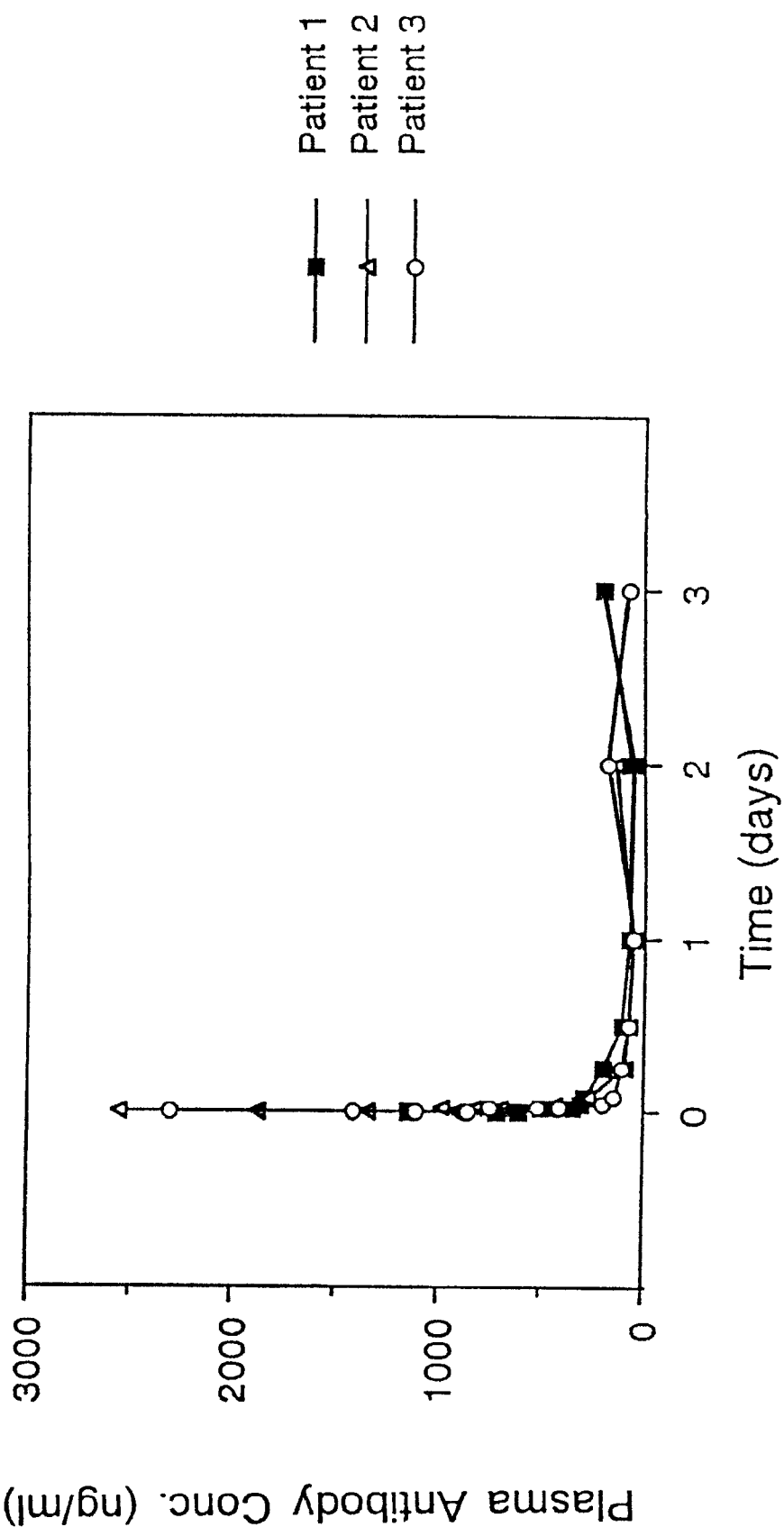
FIG. 4 is a graphic illustration of a plot of the plasma antibody concentration (ng/mL) versus time (days) which demonstrates the rapid initial clearance of c7E3 Fab ($\gamma_1$, κ) from the plasma in three patients with stable coronary disease, following a 0.25-mg/kg dose of c7E3 Fab administered intravenously as a five minute infusion.

If the entire injected dose of 7E3 were detected as free antibody in plasma, the theoretical maximum antibody concentration would be approximately 6.25 µg/mL (0.25 mg/kg divided by 40 mL of plasma/kg). However, this theoretical maximum concentration would never be attained because of the large component of injected antibody which binds to platelets. In fact, at the earliest measurement time (2 minutes), the average plasma concentration (n=2) of c7E3 Fab was 2.43 µg/mL; this value was the observed maximum plasma concentration ($C_{max}$). The data obtained at subsequent post-injection times show a rapid initial decrease in the plasma concentration of c7E3 Fab. By the 1-hour and 24-hour measurements, the administered antibody remaining in the plasma (n=3) was less than 0.5 µg/mL and 0.1 µg/mL, respectively. A plot of the plasma antibody concentration (ng/mL) versus time data, presented in FIG. 4 graphically demonstrates the rapid initial clearance of c7E3 Fab from the plasma in all three patients.

A preliminary analysis of the pharmacokinetic characteristics of c7E3 Fab fragment was undertaken. Several models, including several mixed (random and fixed effects) linear models as well as standard two-compartmental and non-compartmental models, were used to fit the plasma concentration data. The free plasma antibody data did not adequately fit standard pharmacokinetic models. As the site of action for c7E3 Fab is a receptor located on platelets, it is not unexpected that the plasma concentration of free antibody would not be related to its concentration at its site of action in any simple way. The rapid initial clearance of c7E3 Fab from the plasma reflects, in part, the rapid antibody binding to platelet GPIIb/IIIa receptors. Of the models examined, the random effects linear model was shown to best fit the plasma concentration data. Using this model, preliminary values for the pharmacokinetic parameters, $Cl_p$, $V_d$, and $t_{1/2}$, were determined and are presented in Table 2.

TABLE 2

PHARMACOKINETIC VALUES FOR c7E3 Fab*

| Parameter | Value |
| --- | --- |
| $Cl_p$ (proportion/hr) | 15.6 |
| $V_d$ (L) | 6.8 |
| $t_{1/2}$(hr) | 0.1 (6 min) |

*A random effects linear model was used to fit the data.
$Cl_p$ = Plasma clearance is defined as the rate of decrease in plasma concentration divided by the concentration and is computed as a rate per hour, i.e., if the rate at a given time continued for an hour, the computed rate would be the proportion of drug removed in that hour.
$V_d$ Volume of distribution is defined as the dose administered divided by the measured plasma concentration multiplied by the plasma volume. A 3-L plasma volume typical for a 70-kg person was used in the calculations.
$t_{1/2}$= Elimination half-life.

Urinary Excretion in Humans

Urine samples were collected from three patients with stable coronary disease who were treated intravenously with 0.25-mg/kg of c7E3 Fab (plasma clearance data for these same three patients are discussed above). Total urine output was collected for the following post-injection time periods: 0 to 2 hours, 2 to 6 hours, 6 to 12 hours, and 12 to 24 hours. In addition, a sample of predose urine was also collected. Representative samples of the collected urine samples were analyzed for free 7E3 Fab using a slight modification of the EIA described above. In all cases, no c7E3 Fab was detected in the urine.

Preclinical Toxicology

Preclinical toxicology studies have been performed in 18 monkeys (Cyonomolgus and Rhesus), using chimeric 7E3 Fab. Bolus doses of up to 0.6 mg/kg, followed by infusion of up to 0.8 µg/kg/min for 96 hours were administered (includes studies with heparin, aspirin and recombinant tissue plasminogen activator). In all monkeys, at all doses, in all combinations, 7E3 was safe and well-tolerated, with no significant bleeding complications or other adverse events.

Dose Escalation of Chimeric 7E3 Fab in Stable Angina Patients

A dose escalation study was conducted enrolling 52 stable angina patients (males from 43 to 75 years old) who were off anti-platelet therapy for more than 10 days. A variety of dosing regimens were administered. Patients received either single intravenous bolus injections of 0.15 to 0.30 mg/kg of chimeric 7E3 Fab (20 patients) or a bolus loading followed by continuous intravenous infusions (10 µg/minute) from 12 to 96 hours in duration (32 patients).

Platelet GPIIb/IIIa receptor blockade, platelet aggregation in response to 20 µM ADP (agonist), and bleeding times were determined 2 hours after administration of a bolus dose of c7E3 Fab (0.15–0.30 mg/kg). Receptor blockade and platelet aggregation in response to agonist were determined essentially as described (Gold, H. K. et al., *J. Clin. Invest.*, 86: 651–659 (1990)). Bleeding times were determined by the Simplate method. With increasing doses there was a progressive increase in receptor blockade, as indicated by the percent of receptors blocked (determined from the availability of receptor binding sites). The increase in receptor blockade was paralleled by inhibition of platelet aggregation (measured as a percent of the pre-dose value or baseline), and by an increase in bleeding time.

The peak effect in terms of all three parameters was observed at 0.25 mg/kg. This dose corresponds to a plasma concentration of 5 µg/ml—the concentration at which peak inhibition was seen in a platelet-rich plasma from a normal subject which had been incubated for 15 minutes in an aggregometer cuvette in the presence of increasing concentrations of chimeric 7E3 Fab. (The extent of aggregation of the plasma of the normal subject was measured by the percent of light transmitted through the cuvette. Prior to the addition of an agonist, the plasma was relatively opaque and the percent of light transmitted was set at zero. When the agonist ADP was added to a control sample without antibody, the light transmission progressively increased as aggregation progressed. However, when c7E3 Fab is present, a dose-dependent block of aggregation was observed with complete inhibition at 5 µg/ml c7E3 Fab.)

The duration of action in terms of receptor blockade, inhibition of platelet aggregation, and bleeding time was determined. Peak effects on receptor blockade, platelet agregation, and bleeding time were seen at 2 hours, with gradual recovery over time. Bleeding times returned to near normal values by 6–12 hours.

Because peak receptor blockade and functional inhibition were achieved with 0.25 mg/kg, the duration of platelet inhibition by continuous infusions following this loading dose were assayed to determine if the duration of platelet inhibition could be prolonged. The degree of receptor blockade, inhibition of platelet aggregation, and prolongation of bleeding time were maintained for the duration of continuous infusion in five patients who received a 10 µg/minute continuous infusion of chimeric 7E3 Fab for 72 hours following the 0.25 mg/kg loading dose. Recovery started as soon as the infusion was discontinued. Similar results were seen with 12, 24, 48 and 96 hour infusions.

None of the patients experienced a hypersensitivity reaction. There were no significant treatment related trends in hematology or chemistry laboratory values. Nor were there any major bleeding events. Insignificant bleeding events were rare and included transient mild nose bleed and mild gum oozing in patients with periodontal disease. The results of the trial indicated that chimeric 7E3 Fab can be administered to patients using dosing regimens that produce profound inhibition of platelet function for periods as long as several days.

Immunogenicity Results

In trials with murine 7E3 F(ab')$_2$ and Fab (150 patients), immune responses detected using a sensitive enzyme-linked immunoassay system occurred in 16% (24/150) of the patients. All reactions were of low titer, typically in the range of 1:50 to 1:200. The treatment group included normal volunteers treated with 0.01–0.25 mg/kg murine 7E3 F(ab')$_2$, unstable angina patients treated with 0.05–0.20 mg/kg murine 7E3 F(ab')$_2$, and PTCA patients treated with 0.1 mg/kg murine 7E3 F(ab')$_2$, or 0.15–0.35 mg/kg murine Fab, as well as stable angina patients treated with a single bolus intravenous injection of 0.10–0.30 mg/kg of murine 7E3 Fab, a single bolus dose of either 0.25 or 0.30 mg/kg followed by continuous infusion for 12–36 hours (0.15 µg/kg/min or 10 µg/min) of murine Fab, or with two injections of murine Fab separated by six hours (a single bolus of 0.2 mg/kg–0.30 mg/kg followed by a bolus of 0.05 mg/kg).

Immunogenicity was notably reduced with the human-mouse chimeric 7E3 Fab. None of the 52 patients having stable angina enrolled in the dose escalation study and treated with chimeric 7E3 Fab (see above) showed an immune response to treatment as measured by a similar assay adapted to the chimeric Fab.

Reversibility of Anti-platelet Activity

Chimeric 7E3 Fab ($\gamma_1$, κ) has a slow off rate from platelets and free plasma chimeric 7E3 Fab clears from circulation rapidly (see above). Thus, the antiplatelet effects of chimeric 7E3 are readily reversible by administration of random donor platelets. This reversal or antidote effect by transfusion of platelets has been demonstrated in 2 patients who had received either murine Fab or chimeric Fab and who received random donor platelets during a time when they had nearly complete inhibition of platlet aggregation. Restoration of platelet function was determined by measuring bleeding times. This property is useful in situtations where a bleeding event necessitates restoration of platelet function in a patient.

Example 4

Use of Chimeric 7E3 Antibody in the Prevention of Thrombotic Complications of Elective Coronary Angioplasty Percutaneous transluminal coronary angioplasty (PTCA), by balloon or coronary atherectomy, for example, is an effective method of enlarging the lumen of stenosed coronary arteries. In this procedure, there is an inherent risk of acute coronary occulusion during and after angioplasty. The reported rate of coronary occlusion varies from approximately 3%–6% of elective angioplasty cases (Detre, K. M. et al., *Circulation* 82: 739–750 (1991)), and is the major cause of in-hospital morbidity and mortality. In high risk patients, the incidence of major cardiac events caused by thrombosis is between 10–20%.

Acute coronary occlusion during or immediately after coronary angioplasty appears to be caused by the combination of deep arterial wall injury with resultant partially occlusive "intimal flaps" with or without superimposed thrombus formation, or thrombus formation alone at a site of vessel wall injury. In animal models, reocclusion after successful thrombolysis is preceded by periods of cyclical reductions and restorations in coronary blood flow termed "cyclic flow variations" (CFVs). These CFVs are almost entirely a platelet-mediated phenomenon, and are due to repetitive accumulation and dislodgement of platelet aggregates at sites of coronary stenosis and endothelial injury. Cyclic flow variations after coronary angioplasty have been described in humans. Chimeric 7E3 antibody can be used to inhibit platelet function during angioplasty thereby preventing platelet aggregation and thrombosis. Chimeric 7E3 antibody is particularly useful in patients at high risk of thrombotic occlusion. These patients can be identified on the basis of anatomic (e.g., angiographically defined character-istics of a lesion at a site of stenosis) or clinical risk factors (e.g., myocardial infarction, unstable angina, diabetes, women 65 years or older), which predispose to acute coronary thrombosis and produce the clinical syndromes of acute myocardial infarction, unstable angina or abrupt closure.

Chimeric Anti-platelet Antibody in Elective PTCA

The trial was conducted in two stages. The primary objective of the first stage was to determine the safety and optimal dose of single dose chimeric 7E3 Fab in patients undergoing elective percutaneous transluminal coronary angioplasty (PTCA). Stage II was conducted to evaluate the safety and preliminary efficacy of chimeric 7E3 (c7E3) when administered by bolus infusion followed by various continuous infusion durations. The Stage II study comprised elective coronary angioplasty patients who were at risk for ischemic cardiac complications. High risk patients included those with unstable angina or stable coronary disease with Type B or C lesion specific characteristics. Table 3 lists the definitional criteria for high risk patients, and Table 4 lists the angiographically defined lesion-specific characteristics. Preliminary efficacy was measured as inhibiton of platelet function and prevention of thrombotic complications. Men, between 18 and 76 years of age, and women not of child bearing potential, between 18 and 76 years of age, were eligible to enroll in both stages of the trial.

TABLE 3

ENROLLMENT CRITERIA FOR PATIENTS AT HIGH RISK FOR ISCHEMIC COMPLICATIONS

Moderately high risk:

1) Unstable angina with no lesion-specific characteristic defined.
2) A stenosis with a single Type B lesion-specific characteristic.

Highest risk:

1) stenosis with ≧ two Type B lesion-specific characteristics.
2) Unstable angina with a stenosis with at least one Type B lesion-specific characteristic.
3) Diabetes mellitus with a stenosis with at least one Type B lesion-specific characteristic.
4) Women ≧ 65 years of age with a stenosis with at least one Type B lesion-specific characteristic.
5) A stenosis with at least one Type C lesion-specific characteristic.

TABLE 4

LESION-SPECIFIC CHARACTERISTICS

Type A Lesions (high success, >85%; low risk)

| | |
|---|---|
| -Discrete (<10 mm length) | -Little or no calcification |
| -Concentric | -Less than totally occlusive |
| -Readily accessible | -Not ostial in location |
| -Nonangulated segment, <45° | -No major branch involvement |
| -Smooth contour | -Absence of thrombus |

Type B Lesions (moderate success, 60–85%; moderate risk)

| | |
|---|---|
| -Tubular (10–20 mm length) | -Moderate to heavy calcification |
| -Eccentric | -Total occlusions <3 months old |
| -Moderate tortuosity of proximal segment | -Ostial in location |
| -Moderately angulated segment, >45°, <90° | -Bifurcation lesions requiring double guide wires |
| -Irregular contour | -Some thrombus present |

TABLE 4-continued

LESION-SPECIFIC CHARACTERISTICS

Type C Lesions (low success, <60%; high risk)

- -Diffuse
- -Excessive tortuosity of proximal segment
- -Extremely angulated segments >90°
- -Total occlusion >3 months old
- -Inability to protect major side branches
- -Degenerated vein grafts with friable lesions

Stage I

In Stage I, patients were enrolled in groups receiving a single bolus intravenous injection of chimeric 7E3 ($\gamma_1$, $\kappa$) Fab fragment (prepared and formulated as described in Example 3). A total of 15 patients, (3 women and 12 men) were treated. The median age of patients was 62 years (range 46 years to 76 years). A demographic profile is listed in Tables 5A and 5B for all single dose patients and for patients within the individual dose groups.

Five patients (n=5) each received single doses of 0.15 mg/kg, 0.20 mg/kg or 0.25 mg/kg of c7E3 Fab within about 30 minutes prior to elective PTCA in a dose-escalation protocol. All patients were treated with aspirin (standard dose) and fully anticoagulated with heparin (standard dose) at the time of the procedure.

Although the PTCA procedures were classified as elective for Stage I patients, six of the 15 patients had unstable rest angina. The coronary location of the dilatations is summarized in Table 6 (bottom). Seven of the 15 Stage I patients underwent PTCA of one lesion in a single vessel, 6 underwent multi-lesion PTCA in a single vessel, and 2 patients had multi-vessel PTCA performed (Table 6).

The efficacy criteria for obtaining the optimal single dose of c7E3 were prospectively defined as the minimum dose that achieved median values of the following at 2 hours post-infusion: (1) prolongation of bleeding time of at least 20 minutes; (2) blockade of GPIIb/IIIa receptors such that there were greater than 80% of baseline receptor sites blocked; and (3) an inhibition of platelet aggregation in response to 20 $\mu$M ADP to $\leq$20% of baseline.

TABLE 5A

CHIMERIC 7E3 ANTI-PLATELET ANTIBODY
Patient Classification of Age, Weight, Height, Sex and Race

|  | Continuous | Control | Single Dose |
|---|---|---|---|
| TOTAL PATIENTS | 32 | 9 | 15 |
| AGE |  |  |  |
| Mean | 57.4 | 54.2 | 60.1 |
| Median | 57.0 | 56.0 | 62.0 |
| Minimum | 38 | 37 | 46 |
| Maximum | 76 | 74 | 76 |
| Std. Dev. | 9.7 | 10.5 | 9.7 |
| WEIGHT (kg) |  |  |  |
| Mean | 82.8 | 88.2 | 85.5 |
| Median | 84.8 | 84.2 | 84.0 |
| Minimum | 42.3 | 67.3 | 70.5 |
| Maximum | 113.0 | 122.7 | 107.0 |
| Std. Dev. | 16.6 | 19.0 | 11.1 |
| HEIGHT (cm) |  |  |  |
| Mean | 171.2 | 176.7 | 173.6 |
| Median | 172.8 | 177.8 | 175.2 |
| Minimum | 152.4 | 157.5 | 160.0 |
| Maximum | 185.0 | 185.4 | 188.0 |
| Std. Dev. | 7.9 | 8.8 | 7.8 |
| SEX |  |  |  |
| Female | 8 | 1 | 3 |
| Male | 24 | 8 | 12 |
| RACE |  |  |  |
|  | 0 | 0 | 1 |
| White | 26 | 8 | 11 |
| Black | 5 | 1 | 2 |
| Asian | 0 | 0 | 1 |
| Hispanic | 1 | 0 | 0 |

TABLE 5B

CHIMERIC 7E3 ANTI-PLATELET ANTIBODY
Patient Classification of Age, Weight, Height, Sex and Race

|  | 0.15 mg/kg 7E3 | 0.20 mg/kg 7E3 | 0.25 mg/kg 7E3 | 0.25 mg/kg 7E3* 10 mcg/min for 6 hrs | 0.25 mg/kg 7E3* 10 mcg/mg for 12 hrs | 0.25 mg/kg 7E3* 10 mcg/min for 24 hrs | Placebo |
|---|---|---|---|---|---|---|---|
| TOTAL PATIENTS | 5 | 5 | 5 | 11 | 11 | 10 | 9 |
| AGE |  |  |  |  |  |  |  |
| Mean | 60.6 | 57.2 | 62.6 | 59.1 | 55.0 | 58.1 | 54.2 |
| Median | 63.0 | 56.0 | 65.0 | 60.0 | 53.0 | 58.5 | 58.0 |
| Minimum | 47 | 46 | 51 | 40 | 42 | 38 | 37 |
| Maximum | 73 | 68 | 76 | 76 | 73 | 75 | 74 |
| Std. Dev. | 10.5 | 8.3 | 11.3 | 10.5 | 8.9 | 10.3 | 10.5 |
| WEIGHT (kg) |  |  |  |  |  |  |  |
| Mean | 83.8 | 80.5 | 92.2 | 85.8 | 83.8 | 78.3 | 88.2 |
| Median | 76.3 | 78.0 | 96.0 | 89.0 | 85.0 | 79.9 | 84.2 |
| Minimum | 74.5 | 70.5 | 82.0 | 60.4 | 42.3 | 62.3 | 67.3 |
| Maximum | 107.0 | 95.0 | 99.1 | 113.0 | 111.8 | 95.0 | 122.7 |
| Std. Dev. | 13.8 | 9.5 | 7.7 | 17.8 | 19.6 | 10.7 | 19.0 |

TABLE 5B-continued

CHIMERIC 7E3 ANTI-PLATELET ANTIBODY
Patient Classification of Age, Weight, Height, Sex and Race

| | 0.15 mg/kg 7E3 | 0.20 mg/kg 7E3 | 0.25 mg/kg 7E3 | 0.25 mg/kg 7E3* 10 mcg/min for 6 hrs | 0.25 mg/kg 7E3* 10 mcg/mg for 12 hrs | 0.25 mg/kg 7E3* 10 mcg/min for 24 hrs | Placebo |
|---|---|---|---|---|---|---|---|
| HEIGHT (cm) | | | | | | | |
| Mean | 170.8 | 171.9 | 178.1 | 169.3 | 170.9 | 173.7 | 176.7 |
| Median | 173.0 | 175.2 | 177.8 | 167.6 | 172.7 | 175.2 | 177.8 |
| Minimum | 160.0 | 160.8 | 169.0 | 157.5 | 152.4 | 165.1 | 157.5 |
| Maximum | 177.8 | 182.9 | 188.0 | 177.8 | 185.0 | 180.3 | 185.4 |
| Std. Dev. | 7.0 | 8.8 | 7.0 | 6.4 | 10.8 | 5.4 | 8.8 |
| SEX | | | | | | | |
| Female | 3 | 0 | 0 | 3 | 4 | 1 | 1 |
| Male | 2 | 5 | 5 | 8 | 7 | 9 | 8 |
| RACE | | | | | | | |
| | 0 | 0 | 1 | 0 | 0 | 0 | 0 |
| White | 3 | 4 | 4 | 8 | 9 | 9 | 8 |
| Black | 2 | 0 | 0 | 3 | 2 | 0 | 1 |
| Asian | 0 | 1 | 0 | 0 | 0 | 0 | 0 |
| Hispanic | 0 | 0 | 0 | 0 | 0 | 1 | 0 |

TABLE 6

ANGIOGRAPHIC CHARACTERISTICS

| | Control | c7E3 Fab Stage I | c7E3 Fab Stage II |
|---|---|---|---|
| Number of Lesions Attempted: | | | |
| Single vessel/single lesion | 8 | 7 | 21 |
| Single vessel/multilesion | 0 | 6 | 7 |
| Multivessel/single lesion | 1 | 2 | 1 |
| Multivessel/multilesion | 0 | 0 | 2 |
| Unknown | 0 | 0 | 1 |
| Location of Attempted Lesions*: | | | |
| RCA | 3 | 9 | 13 |
| LCX | 4 | 3 | 14 |
| LAD | 3 | 9 | 17 |

*In patients with multivessel disease, both vessels are counted.
RCA = Right coronary artery
LCX = Left circumflex coronary artery
LAD = Left anterior descending coronary artery Stage II In Stage II, patients were treated with a 0.25 mg/kg bolus dose followed by a continuous infusion of 10 μg/min of c7E3 Fab for 6, 12, or 24 hours. A total of 32 patients (8 women and 24 men) were entered into the treatment group of Stage II of the study. The median age of the c7E3 Fab-treated patients was 57 years (range 38–76). Nine control patients (1 woman, 8 men) were entered. The median age of control patients was 56 years (range 37–74). Control patients were high risk patients as defined above, who did not receive c7E3, but were monitored and followed in the same fashion as treated patients. A demographic profile for all Stage II patients and for patients within the individual dose groups is listed in Tables 5A and 5B.

Treatment with c7E3 Fab was initiated 30 minutes prior to balloon inflation for PCTA. Aspirin and heparin were given as clinically indicated, with the recommendation that following angioplasty heparin be given at the rate of 800 units per hour. Eleven patients each were entered into the 6 and 12 hour groups, and ten patients were entered into the 24 hour group.

Of the 32 c7E3 Fab-treated patients, 21 patients underwent PTCA of one lesion in a single vessel, 7 patients underwent multi-lesion PTCA in a single vessel, and 3 patients had multi-vessel PTCA performed (Table 6). The type of PTCA was not specified in one patient. The coronary location of the dilatations for stage II patients is summarized in Table 6. Of the 9 control patients, 8 underwent PTCA of one lesion in a single vessel, and one patient had multi-vessel PTCA. The 32 c7E3 Fab-treated patients and the 9 control patients had clinical or angiographic characteristics that would classify them as high risk for ischemic cardiac complications of PTCA. Two c7E3 Fab-treated patients and one control patient had unspecified risk factors. The remaining 30 c7E3 Fab-treated patients and 8 contol patients had at least one identifiable clinical feature or angiographic characteristic placing them at increased risk of ischemic complication, and most had more than one risk factor. Table 7 summarizes these risk factors for the control and c7E3 treatment groups, and individiaul listings of risk factors by patient within each dose group are presented in Tables 8A through 8D.

TABLE 7

HIGH RISK CHARACTERISTICS
Stage II

| Risk Factors | Control (n = 9) | c7E3 Treatment (n = 32) |
|---|---|---|
| One Type B characteristic | 5[1] | 4 |
| Two or more Type B characteristics | 1[2] | 7[3] |
| One Type C characteristic | 0 | 2 |
| Unstable angina with no lesion characteristics identified | 1 | 1[4] |
| Unstable angina + Type B characteristic | 0 | 8[5] |
| Unstable angina + ≧2 Type B characteristics | 1 | 7[6] |

TABLE 7-continued

HIGH RISK CHARACTERISTICS
Stage II

| Risk Factors | Control (n = 9) | c7E3 Treatment (n = 32) |
| --- | --- | --- |
| Unstable angina + Type C characteristic | 0 | 1 |
| Unspecified risk characteristic | 1 | 2 |

[1] Patient 04-006 had diabetes
[2] This patient (04-007) had diabetes
[3] Patients 03-001 and 02-007 had diabetes
[4] This patient (04-004) had the following additional risk factors: female, age >65, and diabetes
[5] Patients 03-003 and 05-001 had diabetes
[6] Patient 01-018 had the following additional risk factors: female and age >65. Patient 03-002 had diabetes.

TABLE 8A

PREDISPOSING HIGH RISK CHARACTERISTICS
Control Patients

| Patient Number | Type of Risk(s)[1] | Segment[2] |
| --- | --- | --- |
| 01-023 | 1. Unstable angina | LAD |
| 01-024 | 1. One Type B characteristic[3] | LAD |
| 04-006 | 1. Diabetes<br>2. One Type B characteristic (eccentric) | LCX |
| 04-007 | 1. Diabetes<br>2. Two Type B characteristics (eccentric; moderately angulated segment; >45°, <90°) | RCA |
| 04-008 | 1. One Type B characteristic (eccentric) | LCX |
| 04-009 | 1. Our Type B characteristic (eccentric) | LCX |
| 01-021 | 1. One Type B characteristic[3] | RCA |
| 01-022 | 1. Unstable angina<br>2. Two Type B characteristics (tubular; irregular contour) | OM |
| 03-005 | 1. Unspecified risk characteristic | RCA |

[1] Potential characteristics listed in Tables 3 and 4
[2] RCA = right coronary artery
LCX = left circumflex coronary artery
LAD = left anterior descending coronary artery
OM = obtuse marginal branches of LCX
[3] Characteristic not designated

TABLE 8B

PREDISPOSING HIGH RISK CHARACTERISTICS
6-Hour Continuous Infusions

| Patient Number | Type of Risk(s)[1] | Segment[2] |
| --- | --- | --- |
| 04-001 | 1. Unstable angina<br>2. One Type B characteristic (eccentric) | RCA |
| 06-001 | 1. Unstable angina<br>2. One Type B characteristic (thrombus) | LCX |
| 06-002 | 1. One Type B characteristic (tubular [10 to 20 mm lesion]) | LAD |
| 01-014 | 1. Unstable angina<br>2. One Type C characteristic (Diffuse >2 cm length) | LAD |
| 01-013 | 1 Unstable angina<br>2. Two Type B characteristics (eccentric, some thrombus) | RCA |
| 01-015 | 1. Two or more Type B characteristics[3] | LAD, LADD |
| 01-017 | 1. One Type B characteristic (eccentric) | LCX |
| 02-005 | 1. Unstable angina<br>2. Three Type B characteristics (tubular, (10 to 20 mm length); irregular contour; ostial in location) | LAD |
| 03-001 | 1. Diabetes<br>2. Four Type B characteristics (eccentric; moderate angulation, >45 °, <90°; irregular contour; moderate to heavy calcification) | LAD |
| 01-012 | 1. One Type C characteristic (Diffuse >2 cm length) | LAD |
| 01-016 | 1. One Type B characteristic (some thrombus) | RCA OM$_n$ |

[1] Potential characteristics listed in Tables 3 and 4
[2] RCA = right coronary artery
LCX = left circumflex coronary artery
LAD = left anterior descending coronary artery
LADD = diagonal branch of LAD
[3] Characteristic not designated
OM$_n$ = obtuse marginal branches of LCX

TABLE 8C

PREDISPOSING HIGH RISK CHARACTERISTICS
12-Hour Continuous Infusion

| Patient Number | Type of Risk(s)[1] | Segment[2] |
| --- | --- | --- |
| 01-018 | 1. Unstable angina<br>2. Female over 65<br>3. Two or more Type B characteristics | OM |
| 01-019 | 1. Unstable angina<br>2. Two or more Type B characteristics | Circumflex |
| 02-006 | 1. Unstable angina<br>2. One Type B characteristic (total occlusion <3 months old) | RCA |
| 02-007 | 1 Diabetes<br>2. Five Type B characteristics (eccentric, moderate tortuosity of proximal segment; moderately angulated segment, >45°, <90°; bifurcation lesions requiring double guidewires; total occlusions <3 mo) | LCX OM$_1$, LADD |
| 03-002 | 1. Unstable angina<br>2. Diabetes<br>3. Two Type B characteristics (moderate tortuosity segment; irregular contour) | LAD |
| 03-003 | 1. Unstable angina<br>2. Diabetes<br>3. One Type B characteristic (irregular contour) | RCA |
| 05-001 | 1. Unstable angina<br>2. Diabetes<br>3. One Type B characteristic[3] (eccentric) | LADD RCA |

TABLE 8C-continued

PREDISPOSING HIGH RISK CHARACTERISTICS
12-Hour Continuous Infusion

| Patient Number | Type of Risk(s)[1] | Segment[2] |
|---|---|---|
| 05-002 | 1. One Type B characteristic (tubular) | RCA |
|  | 2. One Type C characteristic (total occlusion >3 months) | LADD |
| 05-003 | 1. Two Type B characteristics (moderately angulated segment, >45°, <90°; some thrombus) | LAD |
| 06-003 | 1. Unstable angina | RCA |
|  | 2. One Type B characteristic (some thrombus) |  |
| 04-002 | 1. Unstable angina | LCX |
|  | 2. One Type B characteristic (tubular 10 to 20 mm) |  |

[1]Potential characteristics listed in Tables 3 and 4
[2]RCA = right coronary artery
LCX = left circumflex coronary artery
LAD = left anterior descending coronary artery
LADD = diagonal branch of LAD
OM = obtuse marginal branches of LCX
$OM_n$ = obtuse marginal branches of LCX
[3]Characteristic not designated

TABLE 8D

PREDISPOSING HIGH RISK CHARACTERISTICS
24-Hour Continuous Infusion

| Patient Number | Type of Risk(s)[1] | Segment[2] |
|---|---|---|
| 01-020 | 1. Two Type B characteristics (irregular contour, thrombus) | RCA some |
| 02-008 | 1. Unstable angina |  |
|  | 2. Type B characteristics |  |
|  | a) 4 characteristics (tubular; eccentric; moderate tortuosity of proximal segment; irregular contour) | LCX |
|  | b) 3 characteristics (eccentric; moderately angulated segment >45°, <90°) | LCX |
| 05-005 | 1. Unstable angina | RCA |
|  | 2. One Type B characteristic[3] |  |
| 05-006 | 1. Unstable angina | RCA |
|  | 2. One Type C characteristic (diffuse (>2 cm length)) |  |
| 04-003 | 1. Two Type B characteristics (eccentric; bifurcation with double guidewires) | LAD |
| 04-004 | 1. Unstable angina | LAD |
|  | 2. Diabetes |  |
|  | 3. Female over 65 |  |
| 04-005 | 1. Two Type B characteristics (eccentric, some thrombus) | RCA |
| 02-009 | 1. Unstable angina |  |
|  | 2. Type B characteristics |  |
|  | a) 3 characteristics (irregular contour, thrombus; bifurcation lesions requiring double guidewires) | LAD some |
|  | b) 1 characteristic (bifurcation lesions requiring double guidewires) | LAD |
|  | c) 2 characteristics (eccentric; bifurcation lesions requiring double guidewires) | DB |
| 05-004 | 1. One Type B characteristic (bifurcation requiring double guidewires) | $OM_1$ |
|  |  | $OM_2$ |

[1]Potential characteristics listed in Tables 3 and 4
[2]RCA = right coronary artery
LCX = left circumflex coronary artery
LAD = left anterior descending coronary artery
LADD = diagonal branch of LAD
DB =
$OM_n$ = obtuse marginal branches of LCX
[3]Characteristic not designated Inhibition of Platelet Function (Stage I Results)

To assess activity of the chimeric 7E3 Fab in inhibiting platelet function, GPIIb/IIIa receptor binding site availability (recorded as median percent GPIIb/IIIa blocked), median inhibition of agonist-induced platelet aggregation in response to 20 $\mu$M ADP, and median bleeding times, were serially measured. Receptor blockade and platelet aggregation in response to agonist were determined essentially as described (Gold, H. K. et al., *J. Clin. Invest.*, 86: 651–659 (1990)). For receptor blockade measurements, receptor availability was measured at time 0 and the number of receptors available were taken as 0% receptors blocked (baseline). Other time points are relative to the number of receptors available at baseline or the pre-dose measurement. Bleeding times were determined by the Simplate method.

Figure 5A:
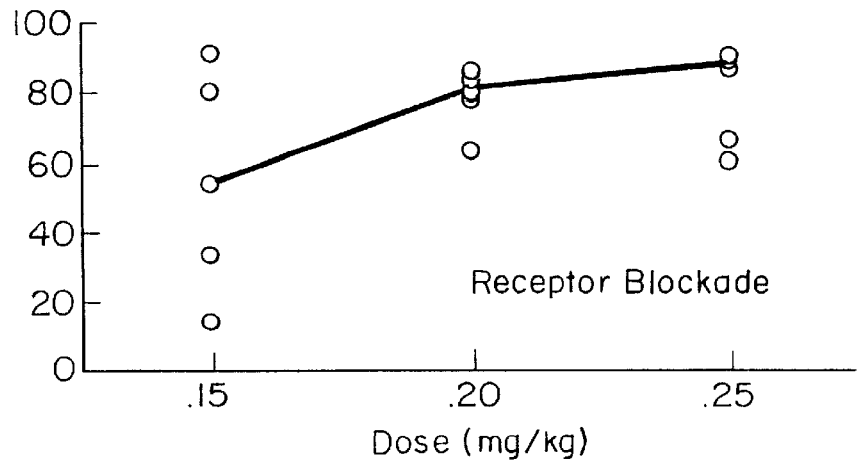
FIGS. 5A–5C are graphs summarizing the effect on platelet activity of a single bolus dose of chimeric 7E3 Fab (0.15 mg/kg, 0.20 mg/kg or 0.25 mg/kg) 2 hours after administration of antibody ($\gamma_1$, κ). A dose response is evident when platelet activity is assayed in terms of receptor blockade (FIG. 5A, top), platelet aggregation (FIG. 5B, middle), and bleeding time (FIG. 5C, bottom). The lines represent median values.
Figure 5B:
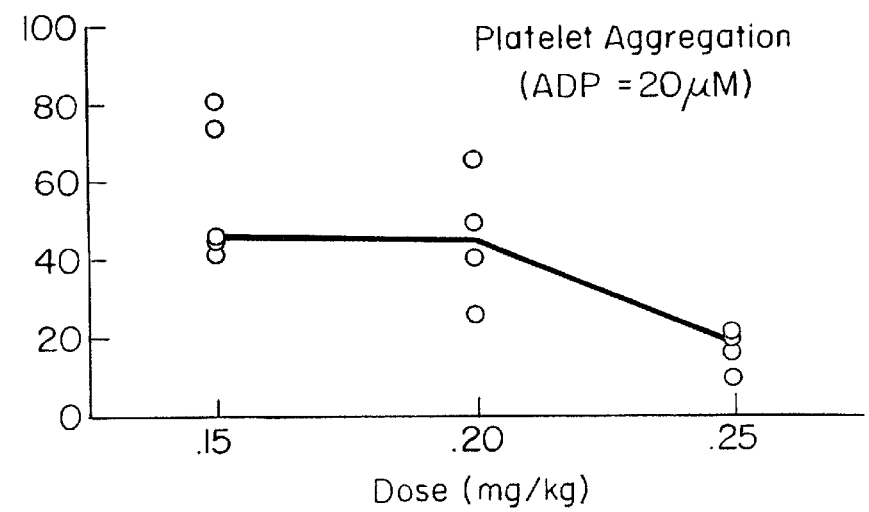
Figure 5C:
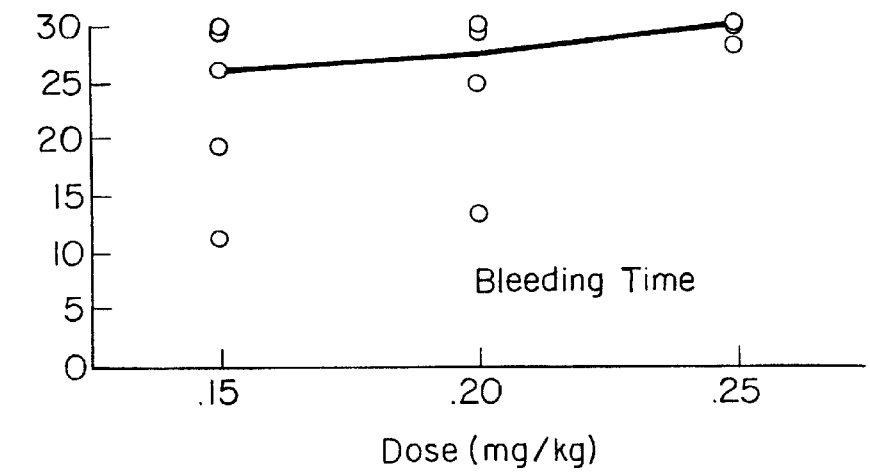

FIGS. 5A–5C summarize the dose response 2 hours following a single bolus dose of chimeric 7E3 Fab, in terms of receptor blockade (FIG. 5A), platelet aggregation (FIG. 5B), and bleeding time (FIG. 5C). The solid lines in FIGS. 5A–5C indicate the median values of the 5 patients studied at each dose group. With increasing doses of c7E3 Fab there was a progressive increase in receptor blockade as shown in percent of receptors that are blocked (FIG. 5A). The median number of receptors blocked at two hours was 53.8% for the 0.15 mg/kg, 80.2% for the 0.20 mg/kg, and 86.6% for the 0.25 mg/kg dose groups. The increase in receptor blockade was paralleled by inhibition of platelet aggregation, depicted as a percent of the pre-dose value (FIG. 5B). Median platelet aggregation at 2 hours was 46.1%, 44.6%, 17.9% of baseline for the 0.15 mg/kg, 0.20 mg/kg, and 0.25 mg/kg dose groups, respectively. Likewise, a dose-related prolongation of bleeding time was seen at 2 hours post-infusion (bleeding time measurements were truncated at 30 minutes; FIG. 5C). The median bleeding times were 26.0 minutes, 27.5 minutes, and 30 minutes for the 0.15 mg/kg, 0.20 mg/kg, and 0.25 mg/kg doses, respectively. Under the conditions used, and as measured by these assays, the optimal dose for anti-platelet activity was determined to be 0.25 mg/kg.

Figure 6A:
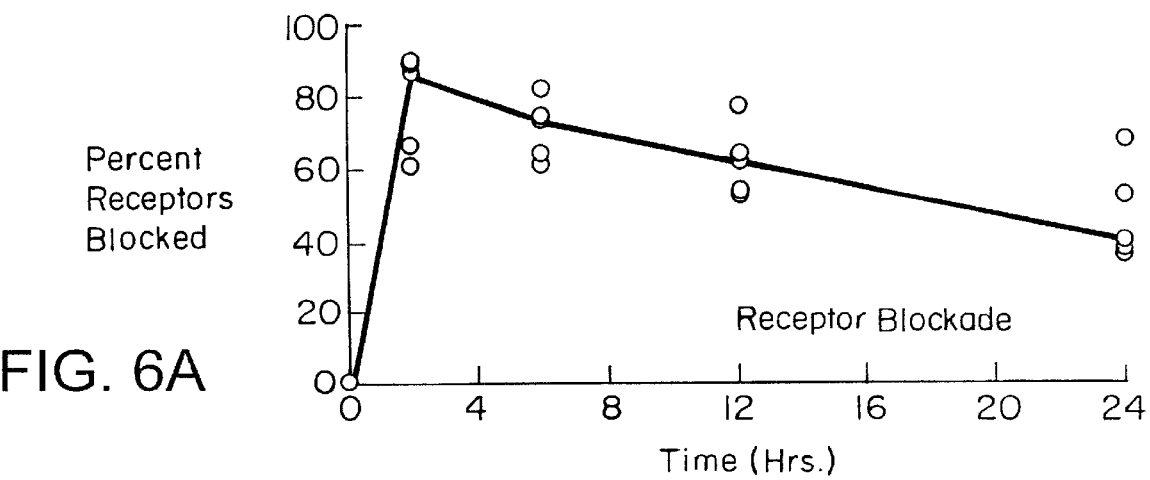
FIGS. 6A–6C are graphs illustrating of the duration of anti-platelet effect of chimeric 7E3 Fab ($\gamma_1$, κ) administered prior to angioplasty in a bolus dose of 0.25 mg/kg. The lines indicate the median values from time zero at baseline through 24 hours for receptor blockade (FIG. 6A, top), platelet aggregation (FIG. 6B, middle), and bleeding time (FIG. 6C, bottom).
Figure 6B:
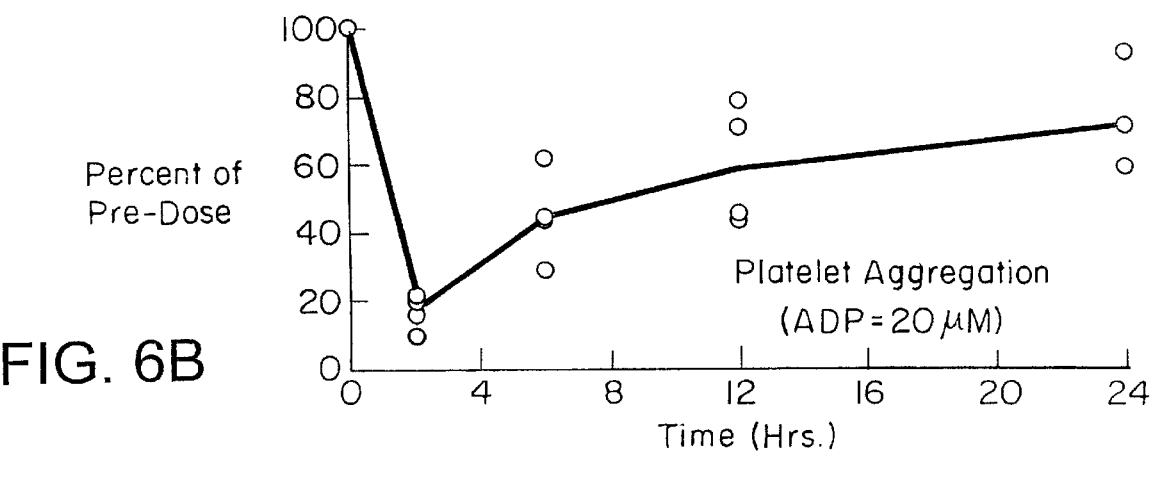
Figure 6C:
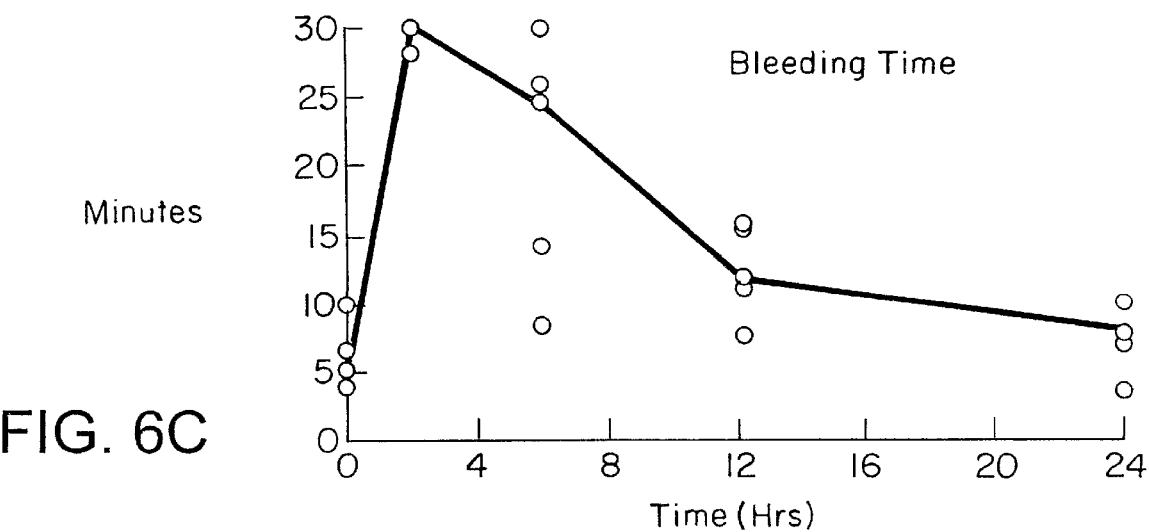

FIGS. 6A–6C show the duration of action following a single bolus dose of 0.25 mg/kg, the dose at which maximum platelet effects were seen. The lines indicate the median values from time zero (baseline) through 24 hours, as shown on the x-axis, in terms of receptor blockade in the top panel (FIG. 6A), platelet aggregation in the middle panel (FIG. 6B), and bleeding time in the bottom panel (FIG. 6C).

Peak effects on receptor blockade, platelet aggregation, and bleeding time are seen at 2 hours, with gradual recovery over time. Bleeding times return to near normal values by 12 hours. None of the patients experienced thrombocytopenia.

Inhibition of Platelet Function (Stage II Results)

Figure 7A:
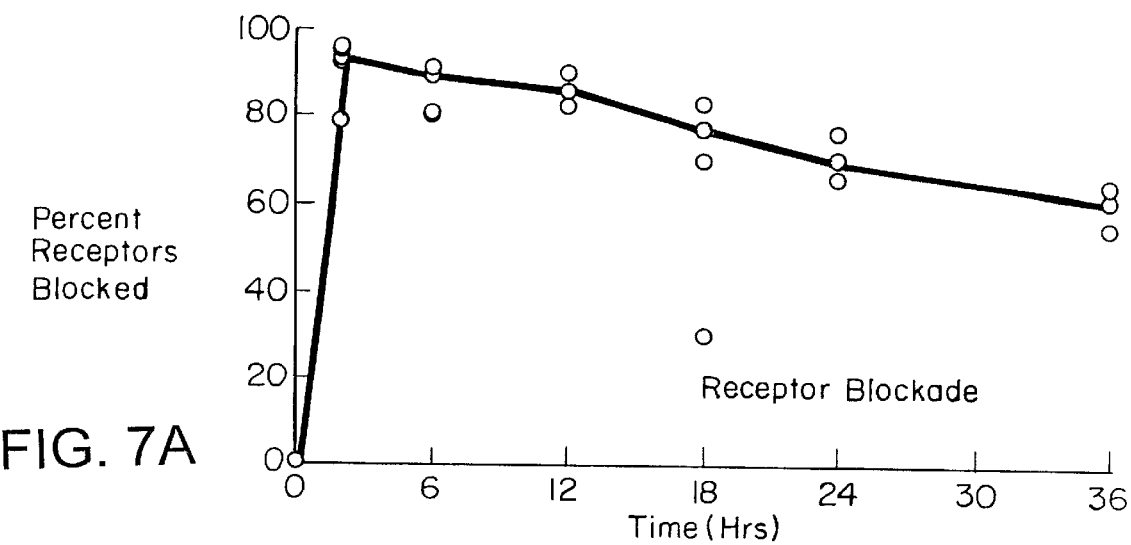
FIGS. 7A–7C are graphs summarizing the anti-platelet activity of a 0.25 mg/kg bolus dose followed by a 12 hour continuous infusion (10 μg/minute) of chimeric 7E3 Fab ($\gamma_1$, κ) in 11 patients. The lines represent median values determined for percent receptor blockade (FIG. 7A, top), percent of pre-dose (baseline at time zero) platelet aggregation (FIG. 7B, middle), and bleeding times (FIG. 7C, bottom).
Figure 7B:
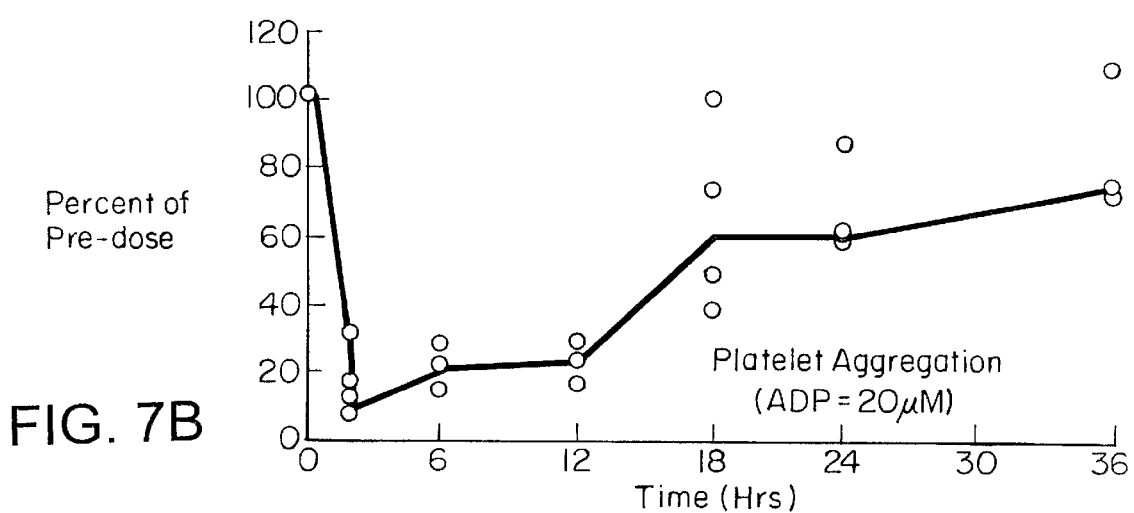
Figure 7C:
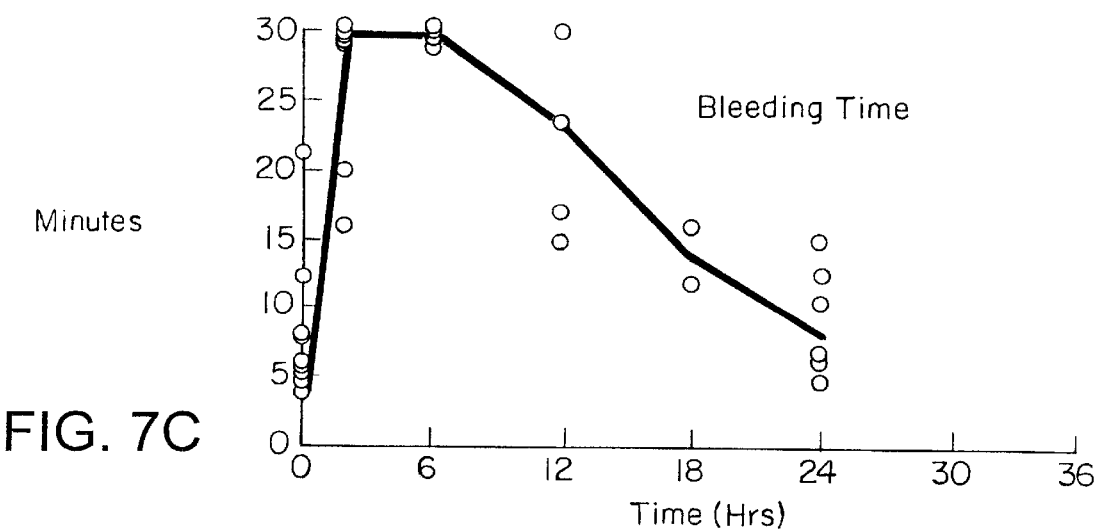

In Stage II, GPIIb/IIIa receptor and platelet aggregation data were not obtained in all patients, and only two patients in the 24 hour infusion had these studies performed. Therefore, only the 6 and 12 hour data are summarized. In both the 6-hour and 12-hour infusion groups, median receptor blockade was maintained to greater than 80% of baseline through the duration of infusion. Median 20 $\mu$M ADP-induced platelet aggregation for the 6 and 12-hour infusion groups was 13% and 15% of baseline at 2 hours, respectively, and in the 12 hour group remained below 25% for the duration of the infusion. The 2-hour median bleeding time for all three infusion durations was greater than 30 minutes. FIGS. 7A–7C review the results observed in patients who received a 10 $\mu$g/minute continuous infusion of chimeric 7E3 Fab for 12 hours following the 0.25 mg/kg loading dose. The lines represent the median values. The degree of receptor blockade, inhibition of platelet aggregation, and prolongation of bleeding time are maintained for the entire duration of the infusion, with recovery starting as soon as the infusion is discontinued.

TABLE 9

MEDIAN DATA FROM FIGS. 7A–7C
0.25 mg/kg + 10 $\mu$g/min for 12 hours

| Time following On-set of infusion Hours | Median Bleeding Time Minutes | Median Aggregation % Baseline | Median Binding % Baseline |
|---|---|---|---|
| 0 | 5.5 | 100 | 0.0 |
| 2 | 30 | 14.7 | 93.5 |
| 6 | 30 | 22.4 | 89.1 |
| 12 | 23.5 | 24.4 | 85.6 |
| 18 | 13.9 | 61.1 | 72.9 |
| 24 | 8.6 | 60.9 | 69.2 |
| 36 | 14.5 | 75.0 | 60.6 |

Clinical Outcomes of Stage I and Stage II Patients

None of the 47 c7E3 Fab-treated patients experienced a thrombotic event during or after PTCA. All but two of the 47 c7E3 treated patients had a successful PTCA as defined angiographically by a reduction of the lesion(s) to less than 50% luminal diameter narrowing. Of the two unsuccessful dilatations, patient 01-012 had a reduction of a 90% narrowing of the left anterior descending coronary artery to 70%, but further dilation was technically not possible. The second patient, (patient 01-019), reviewed below, had an initially successful dilation, but required intracoronary stent placement for a major longitudinal dissection (without evident thrombus). One of the 9 control patients (01-022) experienced thrombotic abrupt closure 15 minutes into the procedure, requiring emergency coronary artery bypass surgery (CABG), from which he recovered. The other 8 control patients had successful dilatations to 50% or less residual narrowing.

Patient 01-019 (12-hour infusion group) had a balloon dilatation of a 95% lesion of the left circumflex coronary artery with a 50% residual narrowing. After the procedure, the patient experienced an apparent vasovagal episode, leading to bradycardia, hypotension, and transient asystole. He was returned to the catheterization laboratory and had urgent intracoronary stent placement for a persistent major longitudinal dissection. The stent became dislodged in the left main coronary artery, and the patient was sent for emergency coronary artery bypass surgery. According to the investigator, there was no evidence of intracoronary thrombosis angiographically or intraoperatively. This patient also experienced a peri-operative myocardial infarction. The patient recovered and was discharged 8 days after surgery.

There were 3 c7E3 Fab-treated patients who each experienced an isolated episode of chest pain post-PTCA of uncertain significance. Patient 01-009 (0.25 mg/kg single does group) experienced chest pain 9 hours post-c7E3, patient 05-003 (12-hour infusion group) experienced angina 21 hours post-c7E3, and patient 06-003 (12-hour infusion group) experienced angina 2 days post-c7E3. The investigators reported that these episodes of chest pain were unrelated to ischemic symptoms signifying reocclusion.

Patient 02-004 (0.25 mg/kg single does group) experienced prolonged periods of chest pain prior to c7E3 Fab treatment which continued during the PTCA procedure. The following day ECG changes accompanied by elevated cardiac enzymes (drawn the preceding day) indicated that this patient had experienced a peri-procedural non Q-wave myocardial infarction (peak creatinine kinase=462, MB fraction=64).

There was one death in the trial which occurred 52 days after c7E3 Fab admininstration. Patient 06-002 (6-hour infusion group), who had a history of interstitial lung disease, congestive heart failure and unstable angina, underwent successful PTCA of the proximal left anterior descending coronary artery. During the procedure the patient developed sustained ventricular fibrillation, twice requiring electrical defibrillation, but thereafter the procedure proceeded uneventfully. After leaving the catheterization laboratory, the patient developed cyanosis, which initially responded to diuretics and oxygen therapy. However, this patient subsequently developed progressive respiratory impairment and later required ventilatory support. The patient's subsequent hospital course was complicated by sepsis, adult respiratory distress syndrome, anemia (requiring multiple transfusions), and cardiac ischemia. This patient died 52 days post-c7E3 Fab due to multi-system failure.

Safety

Stage I and Stage II Observations

Figure 8:
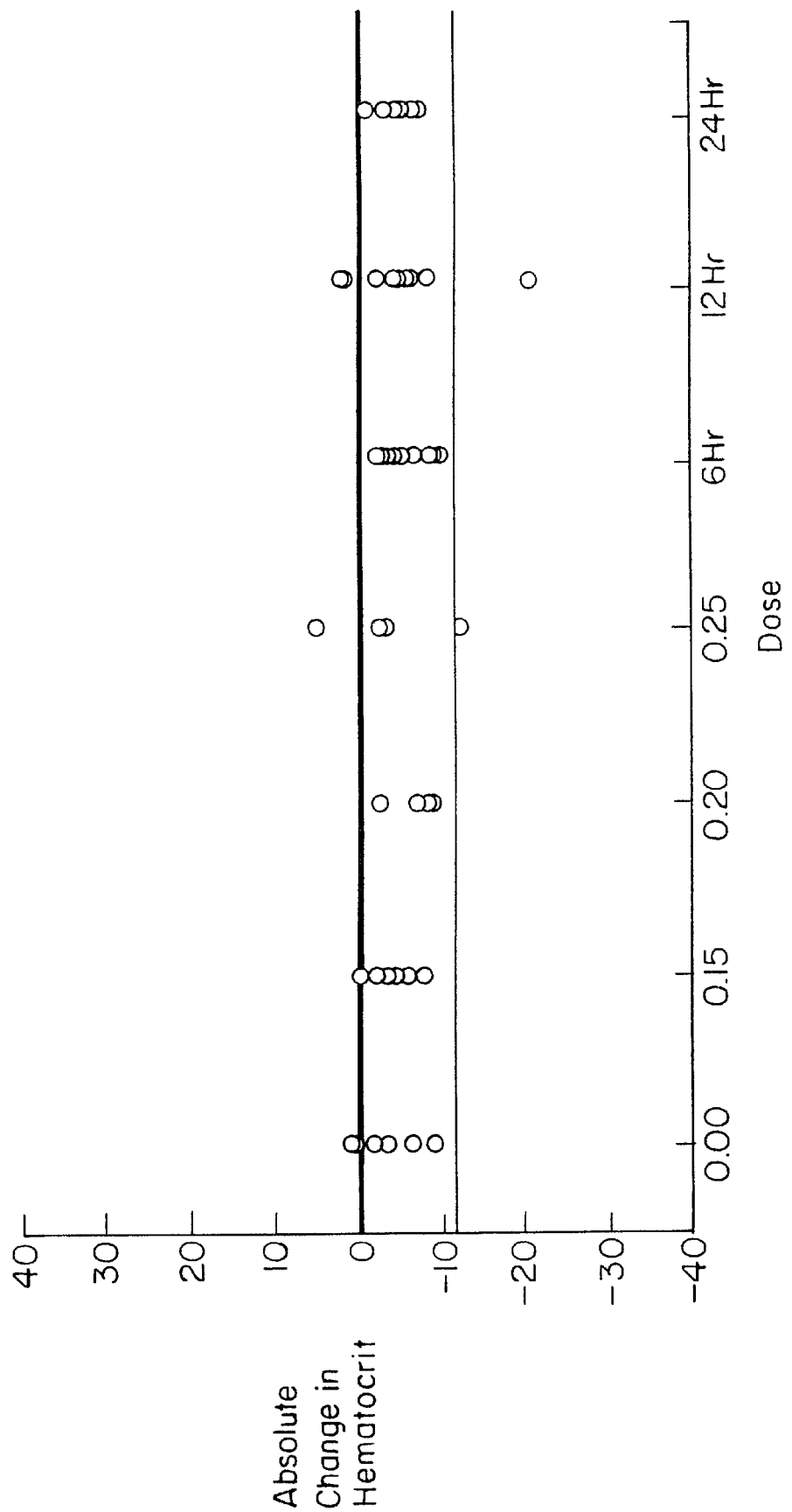
FIG. 8 is an illustration of the absolute change in hematocrit from baseline to a time 24 hours following the end of infusion for 47 patients described in Example 4.

FIG. 8 shows the absolute change in hematocrit from baseline to 24 hours following the end of infusion for all patients by dose group. For reference, a line indicating the zero change point is shown. The hematocrit data from one control patient (01-022) and one c7E3 Fab-treated patient (01-019) are not plotted because both patients required blood transfusions following urgent coronary bypass surgery in the first 24 hours (see below). A second lower line at −12 indicates the change in hematocrit needed to be designated as a minor bleed using the Thrombolysis in Myocardial Infarction (TIMI) criteria (Rao et al., J. Am. Coll. Cardiol. 11: 1–11 (1988)). The changes in hematocrit are similar between the control patients and all c7E3 Fab dose groups. Table 10 summarizes the median change in platelet count at 24 hours following the end of infusion. The change in platelet count in the untreated control and c7E3 Fab-treated groups had similar distributions, with no apparent dose-related effect.

TABLE 10

MEDIAN % CHANGE IN PLATELET COUNT AT 24 HOURS
FOLLOWING THE END OF INFUSION

| Dose | % Change | Range |
|---|---|---|
| Controls (n = 9) | −0.7 | (−20.2, +13.2) |
| 0.15 mg/kg (n = 5) | −17.4 | (−24.5, +19.5) |
| 0.20 mg/kg (n = 5) | −11.6 | (−20.8, +4.7) |
| 0.25 mg/kg (n = 5) | +2.9 | (−8.9, +4.4) |
| 6 hours* (n = 11) | −7.7 | (−28.3, +19.4) |
| 12 hours* (n = 11) | 0.0 | (−24.3, +24.4) |
| 24 hours* (n = 10) | −3.9 | (−9.0, +50.0) |

*Period of infusion (10 μg/min) of c7E3 Fab following a bolus injection of 0.25 mg/kg Discussion of Stage I and Stage II Results Stage I of this study established that c7E3 exhibits the same dose response characteristic in the PTCA population treated with aspirin and heparin as was seen in stable angina patients in a dose escalation trial (Example 3). Chimeric 7E3 produces a dose-dependent blockade of platelet GPIIb/IIIa receptors, and this receptor blockade correlates with inhibition of platelet function. In addition, Stage II results demonstrate that prolonged inhibition of platelet Fab function up to 24 hours can be achieved by a continuous infusion. In all patients, platelet functional recovery begins by 6 to 12 hours after cessation of the infusion, regardless of the duration of infusion.

The clinical outcome of the c7E3-treated patients, using both angiographic and clinical endpoints, was considerably better than expected based on their risk profile. No patient in the c7E3 treatment group experienced a thrombotic event during or after the procedure. In addition, all but 2 patients had angiographically successful procedures. All patients enrolled into Stage II and 6 of the 15 patients enrolled in Stage I were high risk patients on the basis of clinical or angiographic characteristics. An individual clinical factor (such as unstable angina, diabetes, women over age 65 years) or angiographic lesion-specific characteristic (such as type B or C) places a patient at increased risk of complications, and the effect of multiple factors are cumulative. In Stage II, 17 treated patients had unstable angina with or without additional clinical or angiographic lesion-specific risk factors. In addition, 6 patients in Stage I were identified as having unstable angina. Published series have identified unstable angina patients as having a major complication (death, myocardial infarction, urgent coronary bypass surgery, or repeat PTCA) rate of 10 to 15% (De Feyter, P. J.: Editorial. *Am. Heart J.* 118: 860–868 (1989) and Rupprecht, H. J. et al. *Eur Heart J.* 11: 964–973, (1990)). Angiographic characteristics similarly are highly predictive of PTCA complications (Ellis, S. G.: Elective coronary angioplasty: technique and complications. In *Textbook of Interventional Cardiology,* (Ed. E. J. Topol), W. B. Saunders Co., Philadelphia (1990); De Feyter, P. J. et al., *Circulation* 83: 927–936 (1991); Ellis, S. G. and Topol, E. J, *Am. J. Cardiol.* 66: 932–937 (1990); and ACC/AHA Task Force Report: Guidelines for percutaneous transluminal coronary angioplasty. *J. Am. Coll. Cardiol.* 12: 5290545 (1988)). Twenty-nine Stage II c7E3-treated patients met the eligibility criteria by means of lesion-specific characteristics. Of these, 12 patients had one Type B lesion, 14 had 2 or more Type B lesions, and three had Type C lesions. In addition, many of the patients in the trial had multiple lesions dilatated in a single or more than one vessel, which also potentially increases the risk of the procedure (Samson, M. et al., *Am. Heart J.* 120: 1–12 (1990)). On the basis of both the number and severity of high risk angiographically defined risk factors in these patients, ischemic complications would have been expected in the range of 10 to 20% (Ellis, S. G.: Elective coronary angioplasty: technique and complications. In *Textbook of Interventional Cardiology,* (Ed. E. J. Topol), W. B. Saunders Co., Philadelphia (1990); De Feyter, P. J., *Circulation* 83: 927–936 (1991); Ellis, S. G. and Topol, E. J, *Am. J. Cardiol.* 66: 932–937 (1990)).

The control group also was comprised of high risk patients. However, in general, the number and severity of risk factors was lower in the control patients. Five of the 9 control patients had single risk factors of either one type B lesion (4 patients) or unstable angina (1 patient), whereas 26 of 32 Stage II c7E3-treated patients had either a type C lesion or two or more other high risk characteristics. This difference in risk status between the 2 groups is significantly different (Fisher's exact test p=0.018). Interestingly, the control patient with the abrupt closure (patient 01-022, unstable angina with 2 type B characteristics) was one of 3 patients identified as having more than one risk factor (one control patient had unspecified risk characteristics). Thus, whereas one of three control patients at highest risk had a thrombotic event, none of the 26 c7E3 Fab patients in this highest risk category had a thrombotic event.

This study also demonstrates that the potent antiplatelet effects of c7E3 can be achieved safely in patients already being treated with intravenous heparin and oral aspirin. Bleeding events were comparable in the control and c7E3-treated patients with no difference in hematocrit changes from baseline between dosing groups. Other adverse events were infrequent and typically of mild or moderate severity. There was one death in the trial, and this occurred almost 2 months after c7E3 Fab treatment in a patient with interstitial lung disease and heart failure who had progressive respiratory failure following PTCA, complicated by sepsis, adult respiratory distress syndrome, and eventually multiple organ failure.

Finally, none of the twenty patients in whom results were available experienced a human anti-chimeric antibody immune response.

In conclusion, chimeric 7E3 Fab potently inhibits platelet function safely in patients treated with aspirin and intravenous heparin who are undergoing PTCA. The antiplatelet action can be maintained for a long as 24 hours without a significant increase in bleeding risk and without immune system reactivity. Among patients at high risk of thrombotic complications, no thrombotic events occurred in the group treated with c7E3, suggesting that c7E3 can reduce the risk of thrombotic complications in this patient population.

Example 5

Treatment of Abrupt Closure During Coronary Angioplasty

Abrupt coronary arterial closure during coronary angioplasty is the major determinant of morbidity and mortality in this procedure. It occurs in approximately 3%–6% of elective angioplasty cases (Detre, K. M. et al., *Circulation* 82: 739–750 (1991)), but has been noted to occur in up to 20%–40% of patients who undergo angioplasty for unstable angina pectoris or after acute myocardial infarction (Ellis, S. G. et al., *Circulation* 77: 372–279 (1988); DeFeyter, P. J. et al., *Circulation* 83: 927–936 (1991)). The mechanism of abrupt closure is acute thrombosis at the arterial site where angioplasty has created or extended an area of endothelial injury. Usually there are disturbed flow patterns due to altered geometry of the vessel, often from disruption of the plaque material, and there is exposure of subendothelial elements including intimal and often medial dissection. Since initiation of the thrombus requires adhesion and aggregation of platelets, chimeric 7E3 Fab antibody fragment was used for the treatment of abrupt coronary arterial closure complicating a coronary angioplasty procedure.

Case Report

The patient is a 45 year old male physician who had been in excellent health previously. Beginning one week prior to his angioplasty procedure, he had begun to experience chest and neck discomfort. When these symptoms persisted and worsened over several days, he sought the advice of a colleague. An electrocardiogram (EKG) revealed anterior precordial T wave inversions. The patient was then hospitalized in the coronary care unit of a local hospital and placed on intravenous nitroglycerin and heparin, and oral aspirin. Serial Cardiac isoenzyme determinations over the next 24 hours did not reveal elevation above the normal range. Serial EKG recordings over the next two days revealed persistent flattening of the anterior precordial T waves but no evolutionary changes of myocardial infarction. On the second day after hospitalization the patient was taken to the cardiac catheterization laboratory, where left ventriculography revealed overall normal left ventricular function with a very small hypokinetic area in the anterolateral left ventricular wall, and another hypokinetic area in the inferoposterobasilar zone. The left ventricular ejection fraction was 72%. Coronary arteriography demonstrated a left-dominant coronary system with a small and totally occluded right coronary artery. There was a significant stenosis in the mid portion of the left anserior descending (LAD) coronary artery. A small and diffusely diseased diagonal branch originated just distal to the mid LAD stenosis.

The patient was returned to the coronary care unit and remained on intravenous nitroglycerin and heparin for another 48 hours. He was pain free during this time, cardiac isoenzymes did not rise, and daily EKGs revealed only the persistent flattening of the anterior precordial T waves. He was transferred to Hermann hospital (Houston, Tex.) for angioplasty.

Prior to the angioplasty procedure the patient continued to receive intravenous nitroglycerin and heparin, oral aspirin, and he was started on an oral calcium channel blocking agent. The partial thromboplastin time (PTT) had remained in the 70–90 seconds range for several days. At the start of his angioplasty procedure the activated clotting time (ACT) was 173 seconds. The patient received 5000 units heparin intravenously. The left coronary ostium was engaged with a number 8 French JL 3.5 guiding catheter. The LAD coronary artery was visualized in the caudal right anterior oblique and cranial left anterior oblique projections. The LAD was first instrumented with a 0.018 inch Doppler guidewire (Cardiometrics, Inc., Mountain View, Calif.). This guidewire is used by us routinely for flow monitoring in patients at higher risk for abrupt closure. Flow-velocity signals from the LAD proximal and distal to the lesion were recorded. A 2.5 mm coronary balloon catheter (Intrepid, Baxter, Inc., Irvine, Calif.) was advanced over the Doppler guidewire while the wire was held stationary in the coronary artery. The balloon was positioned so that it straddled the LAD lesion. Sequential brief balloon inflations were made to 6 atmospheres pressure. The severity of the stenosis was reduced as visualized by angiography as well as by increase in the flow velocity signal from a peak flow velocity (APV) of 12 cm/sec to 33 cm/sec.

During several minutes of observation following these dilations it was noted that the flow signal began to diminish. A contrast injection revealed renarrowing of the angioplasty site from elastic recoil, plaque disruption, and formation of thrombus. The balloon was reintroduced to the site of the lesion and another balloon inflation was performed. The artery was reexpanded and the flow signal again returned to an APV of 34 cm/sec. During several more minutes of monitoring the signal again declined. Within 5 minutes the signal was quite low, at average peak velocity of 3 cm/sec. The patient began to experience chest pain. The EKG monitor of an anterior precordial lead revealed ST segment elevation. Angiography revealed that the artery was completely occluded. The activated clotting time obtained just a few minutes before was 344 seconds.

Chimeric 7E3 monoclonal antibody Fab fragment specific for the platelet GP IIb/IIIa receptor (c7E3 Fab, $\gamma_1$, $\kappa$) was administered. The dose was 0.25 mg per kilogram given intravenously over 1 minute. Within approximately 1 to 2 minutes after administration of c7E3 Fab, the coronary flow velocity began to increase. An injection of contrast revealed restoration of coronary patency with Trombolysis In Myocardial Infarction Trial Grade-1 (TIMI 1) flow. Over the subsequent 15 minutes coronary flow continued to increase and stabilized at an APV of 23 cm/sec. Several other injections of contrast demonstrated improved coronary flow. The patient's chest pain subsided and the ST segment observed in the monitor lead returned to baseline.

Fifteen minutes after administration of c7E3 Fab, an angiogram was made according to protocol. This angiogram revealed TIMI3 coronary flow. The flow velocity signal at this time was 20 cm/sec. Continuous monitoring through the subsequent 5 minutes revealed no further improvement in the coronary flow. During that time the video replay of the angiogram confirmed that there was a small amount of thrombus still visible at the angioplasty site. For this reason it was decided to administer intracoronary urokinase 250,000 units. This thrombolytic agent was infused over approximately the next 10 minutes. During that time there was no further improvement in flow as measured by the Doppler guidewire. After completion of the intracoronary urokinase infusion, at the 33rd minute after administration of c7E3 Fab, another coronary angiogram was made. The artery was patent with TIMI 3 flow. Some moderate but definite residual stenosis persisted at the lesion site. In addition, it was observed that the thrombus had diminished further in size but had not been completely dissolved. The decision was made to perform another balloon inflation in order to try to reduce the residual stenosis.

The balloon catheter was again advanced over the guidewire to the site of the lesion. A final balloon inflation to 6 atmospheres for 2 minutes was then performed. Then, the balloon catheter was withdrawn while the wire remained in place. The flow signal increased to an APV of 29 cm/sec and remained stable over several minutes. An angiogram demonstrated adequate reduction in the residual stenosis which had been present. The guidewire was then withdrawn proximal to the stenosis and another flow velocity recording was made. The guidewire, balloon catheter and guiding catheter were withdrawn. This completed the procedure.

The patient was then taken to the coronary care unit. He remained on oral aspirin, nitrates, a calcium channel blocking agent, and intravenous heparin for several days in order to keep the PTT in the 70–90 seconds range. Serial EKGs demonstrated resolution of the anterior precordial T wave inversions and all subsequent EKGs were normal. Serial creatine kinase (CK) isoenzyme values were consistently <100 U/L. The platelet count prior to the PTCA procedure was 248,000, and subsequent platelet counts at 2h, 6h, 12h, 24h, and 48h after c7E3 F(ab) administration were 304,000, 279,000, 246,000, 185,000 and 220,000, respectively. Platelet aggregation induced by 10 μM ADP was 73% by optical densitometry prior to the procedure, and subsequent values at 2h, 6h, 12h, 24h, and 48h were 0%, 13%, 26%, 45%, and 51%, respectively. One week after the angioplasty procedure, the patient had a follow-up catheterization. The LAD coronary artery was found to be widely patent with TIMI 3 flow. He was discharged home later that same day.

Discussion of Case Report

In this patient, the combination of 0.25 mg/kg c7E3 Fab intravenously, 250,000 U intracoronary urokinase, and repeat dilatation, successfully treated the acute ischemic coronary syndrome of abrupt closure during coronary angioplasty. These results suggest that antiplatelet therapy that inhibits platelet glycoprotein IIb/IIIa receptor binding and platelet cross-bridging may be efficacious in helping to achieve stable reperfusion of acutely occluded coronary arteries in similar clinical settings.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of antithrombotic therapy, comprising administering to a patient having a thrombus or at risk of thrombus formation, an effective amount of a chimeric immunoglobulin or chimeric immunoglobulin fragment having specificity for glycoprotein IIb/IIIa, said immunoglobulin or immunoglobulin fragment comprising an antigen binding region derived from the 7E3 monoclonal antibody produced by the hybridoma having ATCC accession number HB 8832 or a functional portion of said antigen binding region having specificity for glycoprotein IIb/IIIa and at least a portion of a constant region of human origin.

2. The method of claim 1, wherein said immunoglobulin or immunoglobulin fragment comprises heavy and light chain variable regions of the 7E3 monoclonal antibody produced by the hybridoma having ATCC accession number HB 8832.

3. A method of antithrombotic therapy, comprising administering to a patient having a thrombus or at risk of thrombus formation, an effective amount of a chimeric immunoglobulin fragment having specificity for glycoprotein IIb/IIIa, said immunoglobulin fragment comprising an antigen binding region derived from the 7E3 monoclonal antibody produced by the hybridoma having ATCC accession number HB 8832 or a functional portion of said antigen binding region having specificity for glycoprotein IIb/IIIa and at least a portion of a human constant region.

4. The method of claim 3, wherein said fragment is an Fab, Fab' or F(ab')$_2$ fragment.

5. The method of claim 3, wherein said immunoglobulin fragment comprises heavy and light chain variable regions of the 7E3 monoclonal antibody produced by the hybridoma having ATCC accession number HB 8832.

6. The method of claim 5, wherein said fragment is an Fab fragment.

7. A method of antithrombotic therapy, comprising administering to a patient having a thrombus or at risk of thrombus formation, an effective amount of a chimeric immunoglobulin Fab fragment having specificity for glvcoprotein IIb/IIIa, said immunoglobulin fragment comprising heavy and light chain variable regions derived from the 7E3 monoclonal antibody produced by the hybridoma having ATCC accession number HB 8832, a portion of a human heavy chain constant region and a human light chain constant region.

8. A method of antithrombotic therapy, comprising administering to a patient having a thrombus or at risk of thrombus formation, a thrombolytic agent and a chimeric immunoglobulin or chimeric immunoglobulin fragment having specificity for glycoprotein IIb/IIIa, said chimeric immunoglobulin or chimeric immunoglobulin fragment comprising an antigen binding region derived from the 7E3 monoclonal antibody produced by the hybridoma having ATCC accession number HB 8832 or a functional portion of said antigen binding region having specificity for glycoprotein IIb/IIIa, and at least a portion of a constant region of human origin.

9. The method of claim 8, wherein said immunoglobulin or immunoglobulin fragment comprises heavy and light chain variable regions of the 7E3 monoclonal antibody produced by the hybridoma having ATCC accession number HB 8832.

10. The method of claim 9, wherein a chimeric immunoglobulin fragment is administered.

11. The method of claim 10, wherein said chimeric immunoglobulin fragment is an Fab, Fab' or F(ab')$_2$ fragment.

12. The method of claim 8, wherein a chimeric immunoglobulin fragment is administered.

13. The method of claim 12, wherein said chimeric immunoglobulin fragment is an Fab, Fab' or F(ab')$_2$ fragment.

14. The method of claim 8, wherein the chimeric immunoglobulin or immunoglobulin fragment is administered along with or subsequent to administration of the thrombolytic agent.

15. The method of claim 8, wherein the thrombolytic agent is selected from the group consisting of tissue plasminogen activator, streptokinase, or urokinase.

16. A method of antithrombotic therapy, comprising administering to a patient having a thrombus or at risk of thrombus formation, an effective amount of a thrombolytic agent and a chimeric immunoglobulin Fab fragment having specificity for glycoprotein IIb/IIIa, said immunoglobulin fragment comprising heavy and light chain variable regions derived from the 7E3 monoclonal antibody produced by the hybridoma having ATCC accession number HB 8832, a portion of a human heavy chain constant region and a human light chain constant region.

17. A method of antithrombotic therapy, comprising administering to a patient having a thrombus or at risk of thrombus formation, an effective amount of a chimeric immunoglobulin or chimeric immunoglobulin fragment thereof having specificity for glycoprotein IIb/IIIa, said chimeric immunoglobulin comprising at least one chimeric heavy chain in association with at least one chimeric light chain, said chains comprising antigen binding regions derived from the 7E3 monoclonal antibody produced by the hybridoma having ATCC accession number HB 8832 or functional portions of said antigen binding regions having specificity for glycoprotein IIb/IIIa, and a constant region of human origin.

18. The method of claim 17, wherein the chimeric immunoglobulin or chimeric immunoglobulin fragment thereof is of the IgG1 subclass.

19. The method of claim 18, wherein a chimeric immunoglobulin fragment is administered.

20. The method of claim 19, wherein the fragment is an Fab fragment.

21. A method of antithrombotic therapy, comprising administering to a patient having a thrombus or at risk of thrombus formation, a thrombolytic agent and a chimeric immunoglobulin or chimeric immunoglobulin fragment thereof having specificity for glycoprotein IIb/IIIa, said chimeric immunoglobulin comprising at least one chimeric heavy chain in association with at least one chimeric light chain, said chains comprising antigen binding regions derived from the 7E3 monoclonal antibody produced by the hybridoma having ATCC accession number HB 8832 or functional portions of said antigen binding regions having specificity for glycoprotein IIb/IIIa, and a constant region of human origin.

22. The method of claim 21, wherein the chimeric immunoglobulin or chimeric immunoglobulin fragment thereof is of the IgG1 subclass.

23. The method of claim 22, wherein a chimeric immunoglobulin fragment is administered.

24. The method of claim 23, wherein the fragment is an Fab fragment.

* * * * *

UNITED STATES PATENT AND TRADEMARK OFFICE
CERTIFICATE OF CORRECTION

PATENT NO. : 5,976,532
DATED : November 2, 1999
INVENTOR(S) : Barry S. Coller and David M. Knight It is certified that error appears in the above-indentified patent and that said Letters Patent is hereby corrected as shown below:

Cover page, item [73]: After "Assignee: Centocor, Inc., Malvern, Pa.", add --The Research Foundation of State University of New York, Albany, NY--

Signed and Sealed this

Twenty-seventh Day of June, 2000

*Attest:*

*Attesting Officer*

Q. TODD DICKINSON

*Director of Patents and Trademarks*